US011407797B2

(12) United States Patent
Hudalla, II et al.

(10) Patent No.: US 11,407,797 B2
(45) Date of Patent: Aug. 9, 2022

(54) MODIFIED GAL-1 PROTEINS AND USES THEREOF

(71) Applicant: University of Florida Research Foundation, Incorporated, Gainesville, FL (US)

(72) Inventors: Gregory Allan Hudalla, II, Gainesville, FL (US); Margaret Mary Fettis, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/755,553

(22) PCT Filed: Oct. 10, 2018

(86) PCT No.: PCT/US2018/055213
§ 371 (c)(1),
(2) Date: Apr. 10, 2020

(87) PCT Pub. No.: WO2019/075062
PCT Pub. Date: Apr. 18, 2019

(65) Prior Publication Data
US 2020/0262882 A1 Aug. 20, 2020

Related U.S. Application Data

(60) Provisional application No. 62/570,993, filed on Oct. 11, 2017.

(51) Int. Cl.
C07K 14/47 (2006.01)
A61P 29/00 (2006.01)
A61K 38/00 (2006.01)

(52) U.S. Cl.
CPC .......... *C07K 14/4726* (2013.01); *A61P 29/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 2005/0074865 A1 | 4/2005 | Afeyan et al. | |
| 2005/0220792 A1 | 10/2005 | Agou et al. | |
| 2005/0260222 A1 | 11/2005 | Gupta et al. | |
| 2007/0098701 A1 | 5/2007 | Okano et al. | |
| 2008/0234177 A1 | 9/2008 | Bremer et al. | |
| 2011/0294983 A1 | 12/2011 | Desmet et al. | |
| 2011/0318372 A1 | 12/2011 | Andersen et al. | |
| 2014/0187487 A1 | 7/2014 | Choichet et al. | |
| 2017/0335311 A1 | 11/2017 | Gruskin et al. | |
| 2018/0073007 A9 | 3/2018 | Gruskin et al. | |
| 2019/0218264 A1 | 7/2019 | Hudalla et al. | |

FOREIGN PATENT DOCUMENTS

| | | |
|---|---|---|
| EP | 1748050 | 1/2007 |
| JP | 2005-537032 A | 12/2005 |
| JP | 2009-515520 A | 4/2009 |
| JP | 2011-520783 A | 7/2011 |
| JP | 2012-514616 A | 6/2012 |
| JP | 2015-528514 A | 9/2015 |
| JP | 2016-040260 A | 3/2016 |
| WO | WO 1999/012041 A1 | 3/1999 |
| WO | WO 2003/090780 A1 | 1/2003 |
| WO | WO 2004/019878 A2 | 3/2004 |
| WO | WO 2007/058776 A2 | 5/2007 |
| WO | WO 2009/143843 A1 | 12/2009 |
| WO | WO 2010/078966 A1 | 7/2010 |
| WO | WO 2011/034605 A2 | 3/2011 |
| WO | WO 2014/043708 A1 | 3/2014 |
| WO | WO 2014/089267 A1 | 6/2014 |
| WO | WO 2016/127100 A1 | 8/2016 |
| WO | WO 2016/172319 A1 | 10/2016 |
| WO | WO 2018/067660 A1 | 4/2018 |

OTHER PUBLICATIONS

Nishi et al. "Functional and structural bases of a cysteine-less mutant as a long-lasting substitute for galectin-1," Glycobiology vol. 18 No. 12 pp. 1065-1073, 2008 (Year: 2008).*
U.S. Appl. No. 16/339,585, filed Apr. 4, 2019, Hudalla et al.
PCT/US2018/055213, Jan. 4, 2019, International Search Report and Written Opinion.
PCT/US2018/055213, Apr. 23, 2020, International Preliminary Report on Patentability.
International Search Report and Written Opinion dated Jan. 4, 2019 for Application No. PCT/US2018/055213.
International Preliminary Report on Patentability dated Apr. 23, 2020 for Application No. PCT/US2018/055213.
Brooks et al., Immunomodulatory Factors Galectin-9 and Interferon-Gamma Synergize to Induce Expression of Rate-Limiting Enzymes of the Kynurenine Pathway in the Mouse Hippocampus. Front Immunol. Oct. 17, 2016;7:422. doi: 10.3389/fimmu.2016.00422.
Fettis et al., Engineering Reactive Oxygen Species-Resistant Galectin-1 Dimers with Enhanced Lectin Activity. Bioconjug Chem. Jul. 18, 2018;29(7):2489-2496. doi: 10.1021/acs.bioconjchem.8b00425. Epub Jul. 3, 2018.
Li et al., Enhancement of an Interfacial Biochemical Reaction through Localization of Substrate and Enzyme by an Adaptor Domain. J Phys Chem B. 2010;114(46):15113-8.
Litowski et al., Designing heterdimeric two-stranded alpha-helical coiled-coils. J Biol Chem. Oct. 4, 2002;277(40):37272-9.

(Continued)

*Primary Examiner* — Christina Bradley
(74) *Attorney, Agent, or Firm* — Wolf, Greenfield & Sacks, P.C.

(57) ABSTRACT

Described herein are modified gal1 monomers that can contain one or more mutated cysteines and/or can be pegylated. Also described herein are modified gal1 dimers, trimers, and tetramers that can contain one or more modified gal1 monomers as described herein. Also described herein are pharmaceutical formulations containing a modified gal1 monomer, dimer, trimer, and/or tetramer. Also described herein are methods of making the modified gal1 polypeptides and complexes thereof. Also described herein are methods of using the modified gal1 polypeptides and complexes thereof.

19 Claims, 35 Drawing Sheets

Specification includes a Sequence Listing.

(56) References Cited

OTHER PUBLICATIONS

Liu et al., Expression of immune checkpoint molecules in endometrial carcinoma. Exp. Ther Med. 2015;10(5):1947-52.
Liu et al., Galectins as molulators of tumor progression. Nat. Rev. Cancer. 2005;5(1):29-41.
Nishi et al., Functional and structural bases of a cysteine-less mutant as a long-lasting substitute for galectin-1. Glycobiology. Dec. 2008;18(12):1065-73. doi: 10.1093/glycob/cwn089. Epub Sep. 16, 2008.
Weidle, et al. Fully Human Targeted Cytotoxic Fusion Proteins: New Anticancer Agents on the Horizon. Cancer Genomics Proteomics. 2012;9:119-33.
Wheeldon et al., Substrate channeling as an approach to cascade reactions. Nat Chem. Apr. 8, 2016:4;299-309.
Extended European Search Report for Application No. EP 17859087.3, dated Apr. 8, 2020.
International Search Report and Written Opinion for Application No. PCT/US2017/055076, dated Feb. 21, 2018.
International Preliminary Report on Patentability for Application No. PCT/US2017/055076, dated Apr. 18, 2019.
Invitation to Pay Additional Fees for Application No. PCT/US2020/020532, dated May 21, 2020.
International Search Report and Written Opinion for Application No. PCT/US2020/020532, dated Jul. 24, 2020.
International Preliminary Report on Patentability for Application No. PCT/US2020/020532, dated Sep. 10, 2021.
International Search Report and Written Opinion for Application No. PCT/US2019/058230, dated Feb. 5, 2020.
International Preliminary Report on Patentability for Application No. PCT/US2019/058230, dated May 6, 2021.
[No Author Listed], Plasmid Files. SnapGene. Retrieved from www.snapgene.com/resources/plasmid-files/?set=pgex_vectors_(ge_healthcare)&plasmid=pGEX-4T-1. Accessed on Nov. 4, 2021. 5 pages.
Iken et al., Indoleamine 2,3-dioxygenase and metabolites protect murine lung allografts and impair the calcium mobilization of T cells. Am J Respir Cell Mol Biol. Oct. 2012;47(4):405-16. doi: 10.1165/rcmb.2011-0438OC. Epub Apr. 19, 2012.
Inohara et al., Cytoplasmic and serum galectin-3 in diagnosis of thyroid malignancies. Biochem Biophys Res Commun. Nov. 21, 2008;376(3):605-10. doi: 10.1016/j.bbrc.2008.09.041. Epub Sep. 20, 2008.
Krylov et al., Leucine Zipper. Encyclopedia of Life Sciences. 2001. 7 pages.
Li et al., Rate enhancement of an interfacial biochemical reaction through localization of substrate and enzyme by an adaptor domain. J Phys Chem B. Nov. 25, 2010;114(46):15113-8. doi: 10.1021/jp102820e. Epub Nov. 3, 2010.
Littlejohn et al., Expression and purification of recombinant human indoleamine 2, 3-dioxygenase. Protein Expr Purif. Jun. 2000;19(1):22-9. doi: 10.1006/prep.2000.1214.
Pechar et al., Coiled coil peptides and polymer-peptide conjugates: synthesis, self-assembly, characterization and potential in drug delivery systems. Biomacromolecules. Jul. 14, 2014;15(7):2590-9. doi: 10.1021/bm500436p. Epub Jun. 3, 2014.
Weisel et al., Fibrin Formation, Structure and Properties. Subcell Biochem. 2017;82:405-456. doi: 10.1007/978-3-319-49674-0_13.

\* cited by examiner

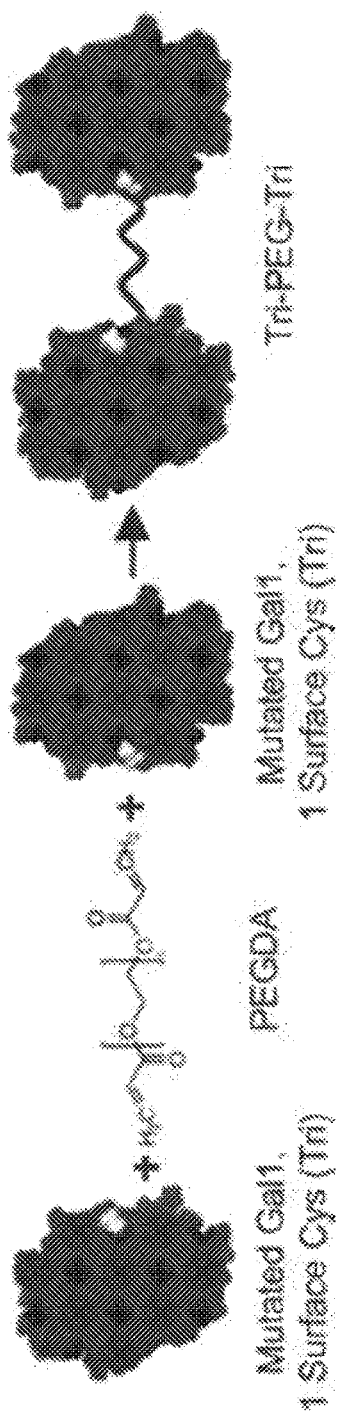
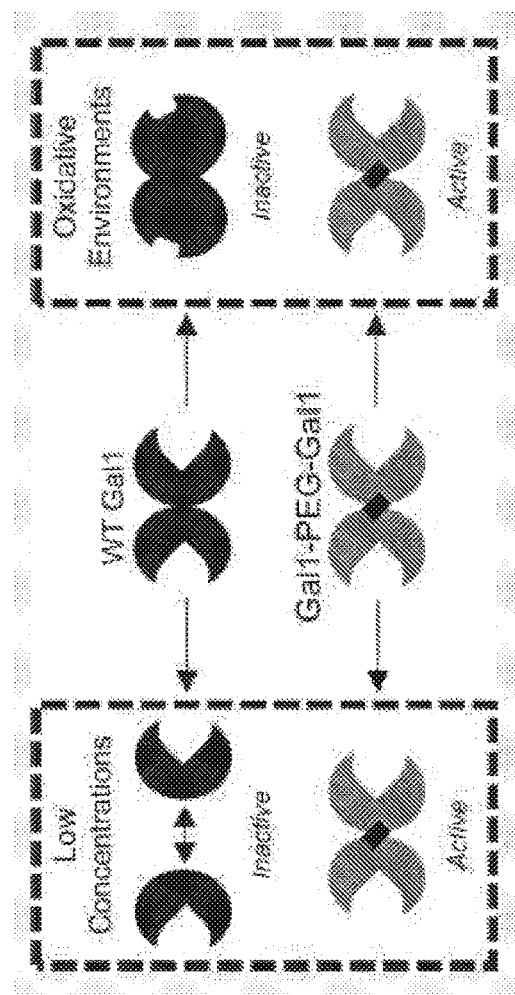
FIG. 1A
FIG. 1B

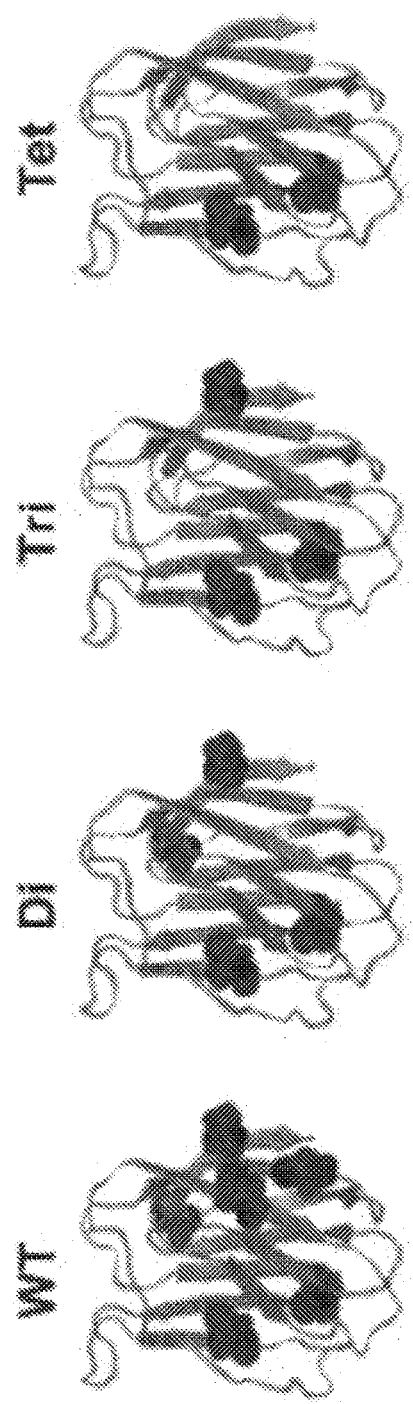
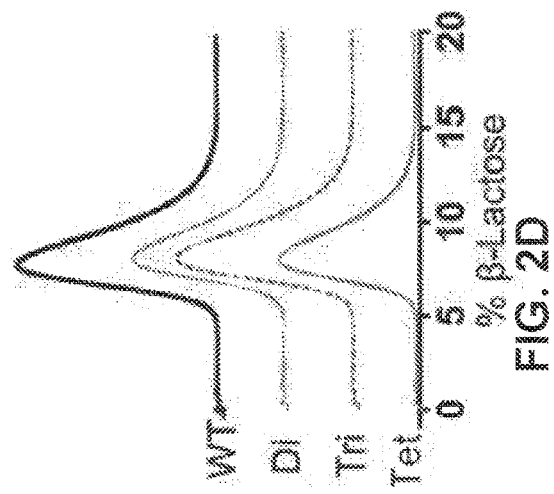
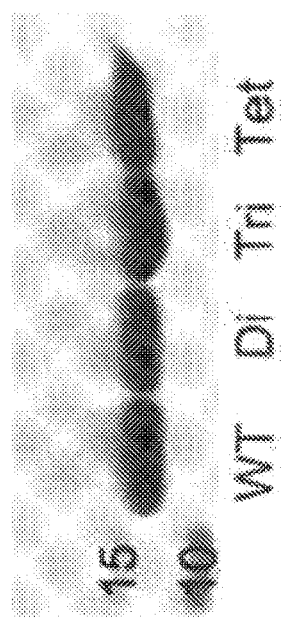
FIG. 2B
FIG. 2C
FIG. 2D

1. WT Galectin-1
2. CS16S/C88S Galectin-1
3. Oxidized C2S/C16S/C88S Galectin-1
4. C2S/C16S/C88S/C130S Galectin-1
N.T. No treatment

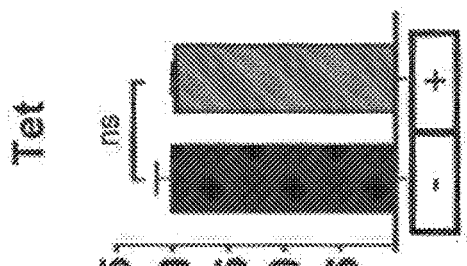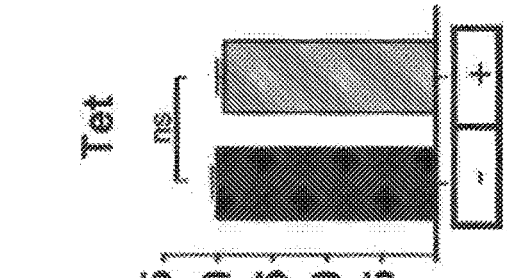
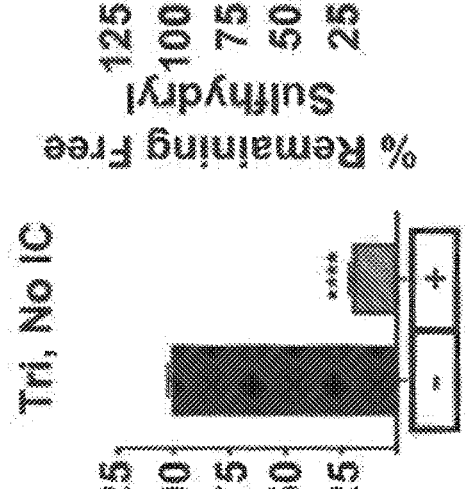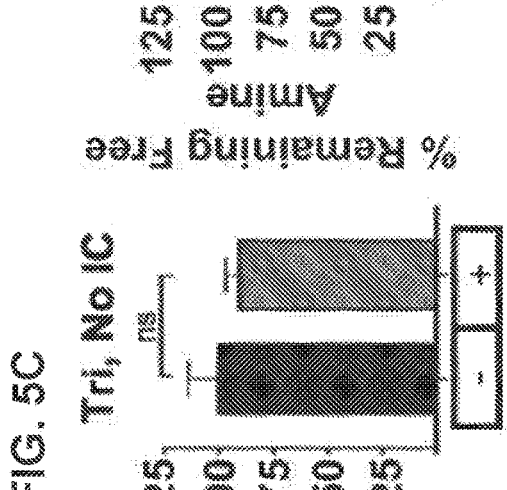
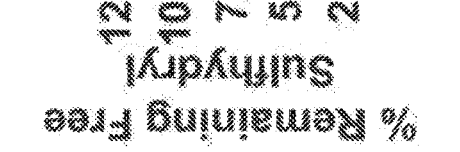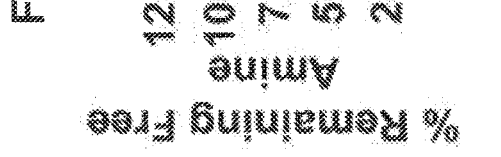
FIG. 5C
FIG. 5D
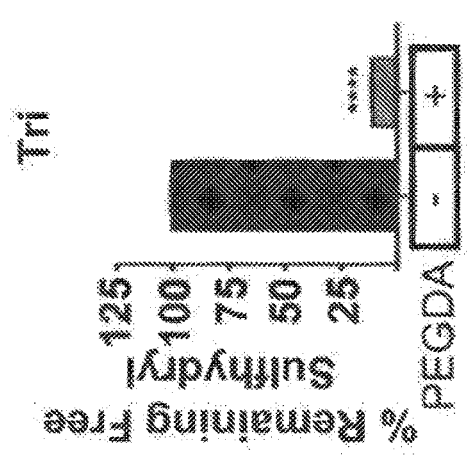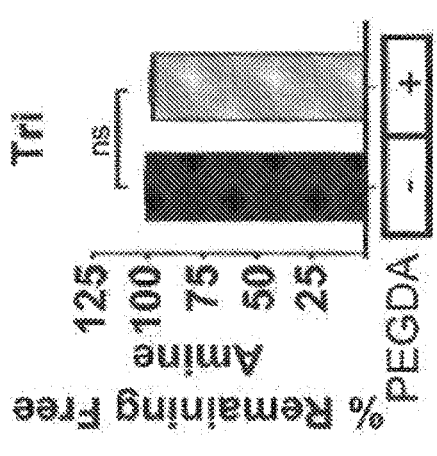

SEQ ID NO: 1 (wild-type gal1 polypeptide, start Met omitted)

AC$_2$GLVASNLNLKPGEC$_{16}$LRVRGEVAPDAK
SFVLNLGKDSNNLC$_{42}$LHFNPRFNAHGDANTIVC$_{60}$
NSKDGGAWGTEQREAVPFQPGSVAEVC$_{88}$ITFDQ
ANLTVKLPDGYEFKFPNRLNLEAINYMAADGDFKI
KC$_{130}$VAFD

FIG. 9

SEQ ID NO: 3       WT Galectin-1 (Gal-1)

MetACGLVASNLNLKPGECLRVRGEVAPDAKSFVLNLGKDSNNLCLHFNP
RFNAHGDANTIVCNSKDGGAWGTEQREAVFPFQPGSVAEVCITFDQANL
TVKLPDGYEFKFPNRLNEAINYMetAADGDFKIKCVAFD Stop SEQ ID NO: 5       Di (C16S/C88S) Gal-1

MetACGLVASNLNLKPGESLRVRGEVAPDAKSFVLNLGKDSNNLCLHFNP
RFNAHGDANTIVCNSKDGGAWGTEQREAVFPFQPGSVAEVSITFDQANL
TVKLPDGYEFKFPNRLNEAINYMetAADGDFKIKCVAFD Stop SEQ ID NO: 7       Tri (C2S/C16S/C88S) Gal-1

MetASGLVASNLNLKPGESLRVRGEVAPDAKSFVLNLGKDSNNLCLHFNP
RFNAHGDANTIVCNSKDGGAWGTEQREAVFPFQPGSVAEVSITFDQANL
TVKLPDGYEFKFPNRLNEAINYMetAADGDFKIKCVAFD Stop

FIG. 9 (ctnd.)

SEQ ID NO: 9    Tet (C2S/C16S/C88S/C130S) Gal-1

MetA S GLVASNLNLKPGE S LRVRGEVAPDAKSFVLNLGKDSNNL S LHFNP
RFNAHGDANTIV C NSKDGAWGTEQREAVFPFQPGSVAEV S ITFDQANL
TVKLPDGYEFKFPNRLNLEAINYMetAADGDFKIKS VAFDStop Tri, No Internal Cysteine Residues (C2S/C16S/C42S/C60S/C88S) Gal-1

SEQ ID NO: 11

MetA S GLVASNLNLKPGE S LRVRGEVAPDAKSFVLNLGKDSNNL S LHFNP
RFNAHGDANTIV S NSKDGAWGTEQREAVFPFQPGSVAEV S ITFDQANL
TVKLPDGYEFKFPNRLNLEAINYMetAADGDFKIK C VAFDStop

FIG. 9 (cntd.)

List of Theoretical kDa's
Gal1: 14.5 kDa
(2) Gal1 + (2) PEGDMal: 35.8 kDa
(2) Gal1 + (3) PEGDMal: 39.2 kDa

SEQUENCE LISTING

<160> NUMBER OF SEQ ID NOS: 15

<210> SEQ ID NO 1
<211> LENGTH: 134
<212> TYPE: PRT
<213> ORGANISM: Artificial Sequence
<220> FEATURE:
<223> OTHER INFORMATION: Wild-type gal1 polypeptide, start Met omitted

<400> SEQUENCE: 1

```
Ala Cys Gly Leu Val Ala Ser Asn Leu Asn Leu Lys Pro Gly Glu Cys
1               5                   10                  15

Leu Arg Val Arg Gly Glu Val Ala Pro Asp Ala Lys Ser Phe Val Leu
            20                  25                  30

Asn Leu Gly Lys Asp Ser Asn Asn Leu Cys Leu His Phe Asn Pro Arg
        35                  40                  45

Phe Asn Ala His Gly Asp Ala Asn Thr Ile Val Cys Asn Ser Lys Asp
    50                  55                  60

Gly Gly Ala Trp Gly Thr Glu Gln Arg Glu Ala Val Phe Pro Phe Gln
65                  70                  75                  80

Pro Gly Ser Val Ala Glu Val Cys Ile Thr Phe Asp Gln Ala Asn Leu
                85                  90                  95

Thr Val Lys Leu Pro Asp Gly Tyr Glu Phe Lys Phe Pro Asn Arg Leu
            100                 105                 110

Asn Leu Glu Ala Ile Asn Tyr Met Ala Ala Asp Gly Asp Phe Lys Ile
        115                 120                 125

Lys Cys Val Ala Phe Asp
        130
```

<210> SEQ ID NO 2
<211> LENGTH: 586
<212> TYPE: DNA
<213> ORGANISM: Artificial Sequence
<220> FEATURE:
<223> OTHER INFORMATION: wild-type gal1 cDNA including polyA tail,
      GenBank Accession No. NM_002305.3

<400> SEQUENCE: 2

```
agttaaaagg gtgggagcgt ccggggcccc atctctctcg ggtggagtct tctgacagct      60
ggtgcgcctg cccgggaaca tcctcctgga ctcaatcatg gcttgtggtc tggtcgccag     120
caacctgaat ctcaaacctg gagagtgcct tcgagtgcga ggcgaggtgg ctcctgacgc     180
taagagcttc gtgctgaacc tgggcaaaga cagcaacaac ctgtgcctgc acttcaaccc     240
tcgcttcaac gcccacggcg acgccaacac catcgtgtgc aacagcaagg acggcggggc     300
ctgggggacc gagcagcggg aggctgtctt tcccttccag cctggaagtg ttgcagaggt     360
gtgcatcacc ttcgaccagg ccaacctgac cgtcaagctg ccagatggat acgaattcaa     420
gttccccaac cgcctcaacc tggaggccat caactacatg gcagctgacg gtgacttcaa     480
gatcaaatgt gtggcctttg actgaaatca gccagcccat ggcccccaat aaaggcagct     540
gcctctgctc cctctgaaaa aaaaaaaaa aaaaaaaaa aaaaaa                      586
```

<210> SEQ ID NO 3
<211> LENGTH: 135
<212> TYPE: PRT
<213> ORGANISM: Artificial Sequence
<220> FEATURE:
<223> OTHER INFORMATION: Wild-type gal1 polypeptide, start Met included.

<400> SEQUENCE: 3

-continued

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135

<210> SEQ ID NO 4
<211> LENGTH: 408
<212> TYPE: DNA
<213> ORGANISM: Artificial Sequence
<220> FEATURE:
<223> OTHER INFORMATION: Wild-1 type gal1 cDNA (encodes SEQ ID NO: 3)

<400> SEQUENCE: 4
atggcttgtg gtctggtcgc agcaacctg aatctcaaac ctggagagtg ccttcgagtg      60
cgaggcgagg tggctcctga cgctaagagc ttcgtgctga acctgggcaa agacagcaac    120
aacctgtgcc tgcacttcaa ccctcgcttc aacgcccacg gcgacgccaa caccatcgtg    180
tgcaacagca aggacggcgg ggcctggggg accgagcagc gggaggctgt ctttcccttc    240
cagcctggaa gtgttgcaga ggtgtgcatc accttcgacc aggccaacct gaccgtcaag    300
ctgccagatg gatacgaatt caagttcccc aaccgcctca acctggaggc catcaactac    360
atggcagctg acggtgactt caagatcaaa tgtgtggcct ttgactga                 408

<210> SEQ ID NO 5
<211> LENGTH: 135
<212> TYPE: PRT
<213> ORGANISM: Artificial Sequence
<220> FEATURE:
<223> OTHER INFORMATION: Modified Gal1 (Di (C16S/C88S) Gal-1) with start
      Met

<400> SEQUENCE: 5

Met Ala Cys Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95
```

```
                    85                  90                  95
Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130             135

<210> SEQ ID NO 6
<211> LENGTH: 408
<212> TYPE: DNA
<213> ORGANISM: Artificial Sequence
<220> FEATURE:
<223> OTHER INFORMATION: Modified Gal1 (Di (C16S/C88S) Gal-1) cDNA
      (encodes SEQ ID NO: 5)

<400> SEQUENCE: 6
atggcttgtg gtctggtcgc cagcaacctg aatctcaaac ctggagagag ccttcgagtg       60
cgaggcgagg tggctcctga cgctaagagc ttcgtgctga acctgggcaa agacagcaac      120
aacctgtgcc tgcacttcaa ccctcgcttc aacgcccacg gcgacgccaa caccatcgtg      180
tgcaacagca aggacggcgg ggcctggggg accgagcagc gggaggctgt ctttcccttc      240
cagcctggaa gtgttgcaga ggtgagcatc accttcgacc aggccaacct gaccgtcaag      300
ctgccagatg gatacgaatt caagttcccc aaccgcctca acctggaggc catcaactac      360
atggcagctg acggtgactt caagatcaaa tgtgtggcct ttgactga                    408

<210> SEQ ID NO 7
<211> LENGTH: 135
<212> TYPE: PRT
<213> ORGANISM: Artificial Sequence
<220> FEATURE:
<223> OTHER INFORMATION: Modified Gal1 (Tri (C2S/C16S/C88S) Gal-1) with
      start Met included

<400> SEQUENCE: 7

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130             135

<210> SEQ ID NO 8
<211> LENGTH: 408
<212> TYPE: DNA
<213> ORGANISM: Artificial Sequence
```

```
<220> FEATURE:
<223> OTHER INFORMATION: Modified Gal1 (Tri (C2S/C16S/C88S) Gal-1) cDNA
      (encodes SEQ ID NO: 7)

<400> SEQUENCE: 8
atggctagtg gtctggtcgc cagcaacctg aatctcaaac ctggagagag ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgagcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct ttgactga                 408

<210> SEQ ID NO 9
<211> LENGTH: 135
<212> TYPE: PRT
<213> ORGANISM: Artificial Sequence
<220> FEATURE:
<223> OTHER INFORMATION: Modified Gal1 (Tetra (C2S/C16S/C88S/C130S)
      Gal-1) start Met included

<400> SEQUENCE: 9

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Leu Cys Leu His Phe Asn Pro
        35                  40                  45

Arg Phe Asn Ala His Gly Asp Ala Asn Thr Ile Val Cys Asn Ser Lys
50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Ser Val Ala Phe Asp
    130                 135

<210> SEQ ID NO 10
<211> LENGTH: 408
<212> TYPE: DNA
<213> ORGANISM: Artificial Sequence
<220> FEATURE:
<223> OTHER INFORMATION: Modified Gal1 (Tetra (C2S/C16S/C88S/C130S)
      Gal-1) cDNA (encodes SEQ ID NO: 9)

<400> SEQUENCE: 10
atggctagtg gtctggtcgc cagcaacctg aatctcaaac ctggagagag ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgagcatc accttcgacc aggccaacct gaccgtcaag     300
```
ctgccagatg gatacgagtt caagttcccc aaccgcctca acctggaggc catcaactac    360
atggcagctg acggtgactt caagatcaaa agtgtggcct ttgactga    408

<210> SEQ ID NO 11
<211> LENGTH: 135
<212> TYPE: PRT
<213> ORGANISM: Artificial Sequence
<220> FEATURE:
<223> OTHER INFORMATION: Modified Gal1 (Tri, No Internal Cysteine
      Residues (C2S/C16S/C42S/C60S/C88S) Gal-1) with start Met included

<400> SEQUENCE: 11

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Ser Leu His Phe Asn Pro
        35                  40                  45

Arg Phe Asn Ala His Gly Asp Ala Asn Thr Ile Val Ser Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135

<210> SEQ ID NO 12
<211> LENGTH: 408
<212> TYPE: DNA
<213> ORGANISM: Artificial Sequence
<220> FEATURE:
<223> OTHER INFORMATION: Modified Gal1 (Tri, No Internal Cysteine
      Residues (C2S/C16S/C42S/C60S/C88S) Gal-1) cDNA (encodes SEQ ID NO:
      11)

<400> SEQUENCE: 12
atggctagtg gtctggtcgc cagcaacctg aatctcaaac ctggagagag ccttcgagtg    60
cgaggcgagg tggctcctga cgctaagagc ttcgtgctga acctgggcaa agacagcaac    120
aacctgagcc tgcacttcaa ccctcgcttc aacgcccacg gcgacgccaa caccatcgtg    180
agcaacagca aggacggcgg ggcctggggg accgagcagc gggaggctgt ctttcccttc    240
cagcctggaa gtgttgcaga ggtgagcatc accttcgacc aggccaacct gaccgtcaag    300
ctgccagatg gatacgaatt caagttcccc aaccgcctca acctggaggc catcaactac    360
atggcagctg acggtgactt caagatcaaa tgtgtggcct ttgactga    408

<210> SEQ ID NO 13
<211> LENGTH: 135
<212> TYPE: PRT
<213> ORGANISM: Artificial Sequence
<220> FEATURE:
<223> OTHER INFORMATION: Modified Gal1 ((C2S/C16S/C42S/C60S/C88S/C130S)
      Gal-1) with start Met included

<400> SEQUENCE: 13

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Ser Leu His Phe Asn Pro
        35                  40                  45

Arg Phe Asn Ala His Gly Asp Ala Asn Thr Ile Val Ser Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Ser Val Ala Phe Asp
        130                 135

<210> SEQ ID NO 14
<211> LENGTH: 135
<212> TYPE: PRT
<213> ORGANISM: Artificial Sequence
<220> FEATURE:
<223> OTHER INFORMATION: Modified Gal 1((C2S/C16S/C42S/C88S) Gal-1) with
      start Met included

<400> SEQUENCE: 14

Met Ala Ser Gly Leu Val Ala Ser Asn Leu Asn Leu Lys Pro Gly Glu
1               5                   10                  15

Ser Leu Arg Val Arg Gly Glu Val Ala Pro Asp Ala Lys Ser Phe Val
            20                  25                  30

Leu Asn Leu Gly Lys Asp Ser Asn Asn Leu Ser Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Ser Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135

<210> SEQ ID NO 15
<211> LENGTH: 135
<212> TYPE: PRT
<213> ORGANISM: Artificial Sequence
<220> FEATURE:
<223> OTHER INFORMATION: Modified Gal 1((C2S/C16S/C60S/C88S) Gal-1) with
      start Met included

<400> SEQUENCE: 15

Met Ala Ser Gly Leu Val Ala Ser Asn Leu Asn Leu Lys Pro Gly Glu
1               5                   10                  15

```
Ser Leu Arg Val Arg Gly Glu Val Ala Pro Asp Ala Lys Ser Phe Val
        20              25              30

Leu Asn Leu Gly Lys Asp Ser Asn Asn Leu Cys Leu His Phe Asn Pro
        35              40              45

Arg Phe Asn Ala His Gly Asp Ala Asn Thr Ile Val Ser Asn Ser Lys
        50              55              60

Asp Gly Gly Ala Trp Gly Thr Glu Gln Arg Glu Ala Val Phe Pro Phe
65              70              75              80

Gln Pro Gly Ser Val Ala Glu Val Ser Ile Thr Phe Asp Gln Ala Asn
            85              90              95

Leu Thr Val Lys Leu Pro Asp Gly Tyr Glu Phe Lys Phe Pro Asn Arg
        100             105             110

Leu Asn Leu Glu Ala Ile Asn Tyr Met Ala Ala Asp Gly Asp Phe Lys
        115             120             125

Ile Lys Cys Val Ala Phe Asp
        130             135
```

MODIFIED GAL-1 PROTEINS AND USES THEREOF

CROSS-REFERENCE TO RELATED APPLICATIONS

This application is a national stage filing under 35 U.S.C. § 371 of international PCT application PCT/US2018/055213, filed Oct. 10, 2018, which claims the benefit of and priority to U.S. Provisional Patent Application No. 62/570,993, filed on Oct. 11, 2017, entitled "MODIFIED GAL-1 PROTEINS AND USES THEREOF," the contents of each of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 14, 2021, is named U119770185US01-SEQ-JOB.txt and is 16,766 bytes in size.

BACKGROUND

Inflammatory diseases includes a vast array of disorders and conditions that can be characterized by inflammation. Inflammatory diseases affect millions of people worldwide and can contribute to significant morbidity and reduced quality of life. As such there exists a need for improved technologies to treat inflammatory diseases and symptoms thereof.

SUMMARY

Described herein are modified gal1 polypeptides that can include one or more mutations as compared to SEQ ID NO: 1, wherein the mutation is selected from the group of: C2S, C16S, C42S, C60S, C88S, C130S, and any combination thereof. In some aspects, the mutations can be C2S, C16S, and C88S. The modified gal1 polypeptide can be resistant to oxidative environments. The modified gal polypeptide can have an amino acid sequence that is 90-100% identical to any one of SEQ ID NOs:5, 7, 9, 11, 13, 14, or 15. The modified gal polypeptide can have an amino acid sequence that is 90-100% identical to any one of SEQ ID NOs: 5, 7, 9, 11, 13, 14, or 15.

Described herein are modified gal1 dimers that can be composed of two modified gal1 polypeptides as described herein, wherein each of the modified gal1 polypeptide can include at least one wild-type gal1 C2, C16, C42, C60, C88, or C130 residue, and wherein the two modified gal1 polypeptides can be crosslinked via a cross-linker between the wild-type gal1 C2, C16, C42, C60, C88 or C130 residue(s) on each of the modified gal1 polypeptides, and wherein the wild-type gal1 has an amino acid sequence that can be 100% identical to SEQ ID NO: 1 when considering non-modified residues. In some aspects, each of the two modified gal1 polypeptides can include a wild-type gal1 C130 residue and a C2S mutation, a C16S mutation, and a C88S mutation as compared to wild-type gal1 of SEQ ID NO: 1. In some aspects, the crosslinker can be poly(ethylene glycol) diacrylate (PEGDA) or poly(ethylene glycol) di-Mal (PEGDMal). In some aspects, an acrylate of the PEGDA or Mal of PEGDMal can interact with the wild-type C2, C16, C88 or C130 residue(s) on each modified gal1 polypeptides In some aspects, the modified gal1 dimer is resistant to oxidative environments.

Also described herein are, modified gal1 tetramers that can be composed of four modified gal1 polypeptides as described herein, wherein each of the modified gal1 polypeptide comprises at least one wild-type gal1 C2, C16, C88 or C130 residue, wherein the four modified gal1 polypeptides are crosslinked via a cross-linker between the wild-type gal1 C2, C16, C88 and/or C130 residue(s) on each modified gal1 polypeptides, and wherein in wild-type gal1 has an amino acid sequence 100% identical to SEQ ID NO: 1 when considering non-modified residues. In some aspects, each of the four modified gal1 polypeptides can include a wild-type gal1 C130 residue and a C2S mutation, a C16S mutation, and a C88S mutation as compared to wild-type gal1 of SEQ ID NO: 1. The cross-linker can be poly(ethylene glycol) tetracrylate (PEGTA) or poly(ethylene glycol) tetra-Mal (PEGTMal). In some aspects, an acrylate of the PEGTA or a Mal of PEGTMal interacts with the wild-type C2, C16, C88 and/or C130 residue(s) on each modified gal1 polypeptides. In some aspects, the modified gal1 tetramer is resistant to oxidative environments.

Also described herein are pharmaceutical formulations that can include a modified gal1 polypeptide as described herein, a modified gal1 dimer as described herein, and/or a modified gal1 tetramer as described herein; and a pharmaceutically acceptable carrier.

Also described herein are methods that can include the step of administering an amount of a modified gal1 polypeptide as described herein, a modified gal1 dimer as described herein, and/or a modified gal1 tetramer as described herein, and/or a pharmaceutical formulation thereof to a subject. The subject can have an inflammatory disease or a symptom thereof. In some aspects, the inflammatory disease can be a chronic inflammatory disease. In some aspects, the inflammatory disease can be an autoimmune disease.

Also described herein are polynucleotides that can include a plurality of nucleotides conjugated together to form a polynucleotide, wherein the polynucleotide encodes a modified gal1 polypeptide as described herein. In some aspects the polynucleotide is about 60 to about 100 percent identical to any one of SEQ ID NOs: 6, 8, 10, or 12.

Also described herein are vectors that can include a polynucleotide as described herein. In some aspects the polynucleotide can include a plurality of nucleotides conjugated together to form a polynucleotide, wherein the polynucleotide encodes a modified gal1 polypeptide as described herein. In some aspects the polynucleotide is about 60 to about 100 percent identical to any one of SEQ ID NOs: 6, 8, 10, or 12.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 1A-1B shows an overview of Tri Gal-1 mutant cross-linking into Tri-PEG-Tri Homodimer and activity in low concentrations and/or oxidative environments. FIG. 1A shows a schematic representation of Gal-1 Tri reacting with PEGDA to form Tri-PEG-Tri. The single surface cysteine on each Tri is highlighted in the protein structure. FIG. 1B shows a schematic representation of activity of a modified Gal1 protein described herein as compared to a wild-type Gal1 protein.

FIGS. 2A-2F show various aspects of Galectin-1 (Gal-1) Cysteine-to-Serine-Mutants. (FIG. 2A) Schematic representation of the primary sequence of wild-type Gal-1 and various Gal-1 Cys-to-Ser mutants. "SH" denotes the sulfhydryl groups present on cysteine residues. SH in gray dashed boxes are located within the protein core, while SH in black solid boxes are on the protein surface. (FIG. 2B) Gal-1 crystal structures highlighting the location of Cys residues in each Gal-1 variant. (FIG. 2C) Scan of SDS-PAGE gel of purified Gal-1 variants. (FIG. 2D) Traces of protein elution from α-lactose:agarose via a soluble β-lactose gradient. FIG. 2E shows a graph demonstrating activity of wild-type (WT) Gal-1 and Gal-1 mutants after oxidation. FIG. 2F shows micrographic images of Jurkat T cells treated with WT or various Gal-1 mutants before oxidation, which can demonstrate lectin activity.

(FIG. 3A) Scan of SDS-PAGE gel of WT Gal-1 and the Di, Tri, and Tet Gal-1 mutants before and after oxidation. (FIG. 3B) Jurkat T cell viability, as assessed via 7AAD staining, following treatment with WT Gal-1 or Di, Tri, and Tet Gal-1 mutants before and after oxidation. (FIG. 3C) Digital micrographs of Jurkat T cells treated with WT Gal-1 or Di, Tri, and Tet Gal-1 mutants before and after oxidation. Scale bars are 50 microm. **** is p≤0.0001, ns is no significance.

(FIG. 4A) Overview of PEGDA and Gal-1 mutant reactions, 1=Tri Gal-1 alone, 2=Tri Gal-1+PEG, 3=Tri Gal-1+PEGDA, 4=Tet Gal-1 alone, 5=Tet Gal-1+PEG, 6=Tet Gal-1+PEGDA. (FIG. 4B) Scan of native PAGE gels of 1-6 after overnight incubation. (FIG. 4C) Plots of free thiol in solutions of 1-6 after overnight incubation. (FIG. 4D) Dynamic light scattering plot of number vs hydrodynamic diameter of 1 and 3. (FIG. 4E) Scan of native PAGE gel of 3 performed at different molar ratios of Tri Gal-1 to PEGDA. **** is p≤0.0001. (FIGS. 4F-4I) Graphs demonstrating MALDI-TOF mass spectrometry results FIGS. 5A-5D can demonstrate that the surface cysteine residue on Tri Gal-1 mutants mediates cross-linking via PEGDA. (FIG. 5C) Plots of free thiol in solutions of Tri Gal-1, Tri, No IC Gal-1, and Tet Gal-1 after overnight incubation with PEGDA. (FIG. 5D) Plots of free amine content of Tri Gal-1, Tri, No IC Gal-1, and Tet Gal-1 after overnight incubation with PEGDA.

(FIG. 6A) Jurkat T cell metabolism following treatment with Gal-1 or Tri-PEG-Tri normalized to untreated cells. (FIG. 6B) Digital micrographs of Jurkat T cells treated with Gal-1 or Tri-PEG-Tri. (FIG. 6C) Metabolic activity of Jurkat T cells treated with Gal-1 or Tri-PEG-Tri in the presence or absence of soluble β-lactose inhibitor. (FIG. 6D) Digital micrographs of cells from experiments in (FIG. 6C). All scale bars are 50 microm. * is p≤0.05,  is p≤0.01, * is p≤0.001, **** is p 0.0001, ns is no significance. FIG. 6E shows microscopic images of Jurkat T cells treated with various concentrations of Tri Gal-1 mutants with and without PEGDA.

In FIG. 8A, grey line is Tet Gal-1 and the Black line is Tri, No Internal Cysteines Gal-1, dotted line is the % β-Lactose over elution volume. The dotted line in FIG. 8B is the peak % β-Lactose.

FIG. 9 shows protein sequences for WT and various Gal-1 mutants described herein. The shaded C residues indicate those residues that can be modified in the mutants. For amino acid counting, residue following the start Met residue is considered amino acid 1. For example, in SEQ ID NO: 3, Residue 1 is A (e.g. $A_1$).

DETAILED DESCRIPTION

Figure 2A:
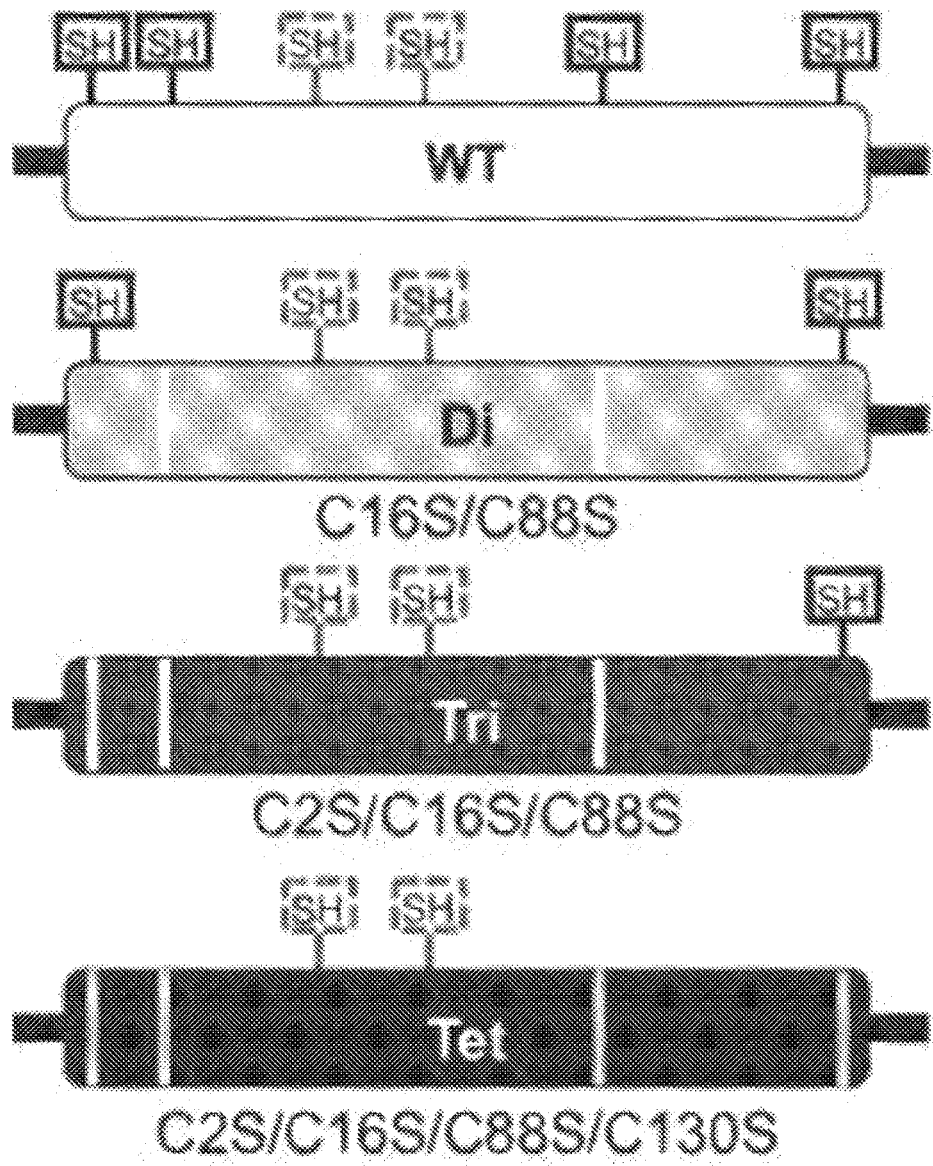

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, immunology, organic chemistry, biochemistry, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

The term "amphiphilic", as used herein, refers to a molecule combining hydrophilic and lipophilic (hydrophobic) properties.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "composition" refers to a combination of active agent and at least one other compound or molecule, inert (for example, a detectable agent or label) or active, such as an adjuvant.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" is an alternative subject or sample used in an experiment for comparison purpose and included to minimize or distinguish the effect of variables other than an independent variable.

As used herein, "chemotherapeutic agent" or "chemotherapeutic" refer to a therapeutic agent utilized to prevent or treat cancer.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" includes nucleic acids/polynucleotides that are made of DNA.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "dose," "unit dose," or "dosage" refers to physically discrete units suitable for use in a subject, each unit containing a predetermined quantity of the targeted effector fusion protein, a composition containing the targeted effector fusion protein, and/or a pharmaceutical formulation thereof calculated to produce the desired response or responses in association with its administration.

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function. "Effective amount" can refer to the amount sufficient to modulate the immune system in a subject and/or treat and/or prevent an inflammatory disease and/or a symptom thereof in a subject.

As used herein, "identity," is a relationship between two or more polypeptide or polynucleotide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure. As used herein, "immunomodulator," refers to an agent, such as a therapeutic agent, which is capable of modulating or regulating one or more immune function or response.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used herein, "matrix" refers to a material, in which one or more specialized structures, molecules, or compositions, are embedded.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "nucleic acid sequence" and "oligonucleotide" also encompasses a nucleic acid and polynucleotide as defined above.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "patient" refers to an organism, host, or subject in need of treatment.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" as used herein refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

As used herein, "protein" as used herein refers to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function. The term protein as used herein can also include peptides. Thus, for example, an "effector protein" can include both effector proteins and effector peptides.

As used herein, "purified" or "purify" is used in reference to a nucleic acid sequence, peptide, or polypeptide that has increased purity relative to the natural environment.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

The terms "treating" and "treatment" as used herein refer generally to obtaining a desired pharmacological and/or physiological effect. The effect may be prophylactic in terms of preventing or partially preventing a disease, symptom or condition thereof, including but not limited to an inflammatory disease or symptom thereof.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "wild-type" is the typical form of an organism, variety, strain, gene, protein, or characteristic as it occurs in nature, as distinguished from mutant forms that may result from selective breeding or transformation with a transgene.

As used herein, "encoding" can refer to the basic biological concept that DNA can be transcribed into RNA, which then can be translated into a polypeptide.

Unless otherwise defined herein, all technical and scientific terms used herein have the same meaning as commonly understood by one of ordinary skill in the art.

DISCUSSION

Galectin-1 (gal1 or gal-1) is a protein that can bind carbohydrates. Gal1 can play a role in a diverse array of biological processes including cell signaling, neuroprotection, angiogenesis, and immune system modulation. Gal1 can selectively target T cell subsets (e.g. Th1 and Th17) to modify the immune response in autoimmune diseases and other inflammatory conditions. Gal1 has an abundance of sulfhydryl (thiol) groups from cysteine residues. In particular, 4 of the cysteine residues are solvent accessible when the gal1 monomer is folded (C2, C16, C88, and C130). These cysteine residues are susceptible to oxidative conditions and can be responsible for de-activating the protein in oxidative environments, which can be typical in sites of inflammation. To retain its immune modulating properties, gal1 must remain in at least a dimer conformation. Dimerization is inhibited in an oxidative environment. Further Gal1 dimerization is reversible, and thus locally high concentrations are needed to maintain protein activity. Given the difficulty with maintaining dimerization in an oxidative environment due to cysteine susceptibility, in vitro results have not translated into in vivo efficacy of gal1.

With that said, described herein are modified gal1 proteins and complexes thereof that can be resistant to oxidative environments. In some aspects, a modified gal1 monomer can contain mutations of 1, 2, 3, or 4 of the 4 solvent accessible cysteine residues. The cysteine(s) can be mutated to serine. In some aspects, a modified gal1 monomer can have a C2S, C16S, and C88S mutation. The modified gal1 monomers can be resistant to oxidation. In some aspects, modified gal1 monomers can be crosslinked to form a modified gal1 dimer or tetramer. In some aspects, the modified gal1 monomers can be crosslinked with poly (ethylene glycol) diacrylate (PEGDA) to form a modified gal1 dimer. In some aspects, the modified gal1 monomers can be crosslinked with a poly(ethylene glycol) tetra-acrylate (PEGTA) to form a modified gal1 tetramer. The modified gal1 dimers and tetramers can be resistant to oxidation. Also provided herein are pharmaceutical formulations containing one or more of the modified gal1 monomers, dimers, and/or tetramers described herein. Also described herein are methods of administering the modified gal1 monomers, dimers, and/or tetramers and/or pharmaceutical formulations thereof to a subject. The subject can have an inflammatory or autoimmune disease.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Modified gal1 Monomers, Dimers, Tetramers, and Pharmaceutical Formulations Thereof Modified gal1 Monomers, Dimers, and Tetramers Described herein are modified gal 1 monomers. Wild-type or native human gal1 can have a sequence according to SEQ ID NO: 1 or 3, which can be encoded by a nucleotide sequence according to SEQ ID NO: 2 or 4, respectively. SEQ ID NOs: 1 and 3 are also shown in FIG. 9.

[[This will be included in the sequence listing along with the other nucleotide sequences in the supplementary material to the Bioconjugate chemistry manuscript]] SEQ ID NO: 2 (wild-type gal1 cDNA including polyA tail, GenBank Accession No. NM_002305.3)

```
AGTTAAAAGGGTGGGAGCGTCCGGGGCCCATCTCTCTCGGGTGGAGTCT

TCTGACAGCTGGTGCGCCTGCCCGGGAACATCCTCCTGGACTCAATCATG

GCTTGTGGTCTGGTCGCCAGCAACCTGAATCTCAAACCTGGAGAGTGCCT

TCGAGTGCGAGGCGAGGTGGCTCCTGACGCTAAGAGCTTCGTGCTGAACC

TGGGCAAAGACAGCAACAACCTGTGCCTGCACTTCAACCCTCGCTTCAAC

GCCCACGGCGACGCCAACACCATCGTGTGCAACAGCAAGGACGGCGGGGC

CTGGGGACCGAGCAGCGGGAGGCTGTOTTTCCCTTCCAGCCTGGAAGTG

TTGCAGAGGTGTGCATCACCTTCGACCAGGCCAACCTGACCGTCAAGCTG

CCAGATGGATACGAATTCAAGTTCCCCAACCGCCTCAACCTGGAGGCCAT

CAACTACATGGCAGCTGACGGTGACTTCAAGATCAAATGTGTGGCCTTTG

ACTGAAATCAGCCAGCCCATGGCCCCCAATAAAGGCAGCTGCCTCTGCTC

CCTCTGAAAAAAAAAAAAAAAAAAAAAAAAAAAAAA
```

The modified gal1 monomer can have a mutated cysteine residue. The modified gal1 monomer can have a C2S, a C16S, a C42S, a C60S, a C88S, a C130S or any combination thereof mutation as compared to SEQ ID NO: 1. The modified gal1 monomer can have a C2S, a C16S, and a C88S mutation as compared to SEQ ID NO: 1. The modified gal1 monomer can have a C16S and a C88S mutation as compared to SEQ ID NO: 1. C2, C16, C42, C60, C88, and C130 are bolded and underlined in SEQ ID NO: 1 as shown in FIG. 9. In some aspects, the wild-type gal1 polypeptide sequence can be 60-100% identical to SEQ ID NO: 1, but still contains C2, C16, C88, and C130. Thus, in this context, in some aspects a wild-type gal polypeptide can be 100% identical except at the positions that is the mutated cysteine residue(s). In some aspects, the modified gal1 monomer can include C2S, C16S, C88S, and C130S mutations; C2S, C16S, and C88S mutations; C16S, C88S, and C130S mutations; C2S, C16S, C42S, and C88S mutations; C2S, C16S, C60S, and C88S mutations; C2S, C16S, C42S, C60S, and C88S mutations; or C16S and C88S mutations. In some aspects, the modified gal1 monomer can have a polypeptide sequence that 80, 81, 82, 83, 84, 85, 86, 87, 88, 89, 90, 91, 92, 93, 94, 95, 96, 7, 98, or 99 to 100 percent identical to any one of SEQ ID NOs: 5, 7, 9, or 11. See e.g. FIG. 9.

Also within the scope of this disclosure are nucleic acid sequences that can encode any of the modified gal1 monomers described herein. In some aspects, the encoding nucleic acid sequence can have a sequence that is about 60, 65, 70, 75, 80, 80, 81, 82, 83, 84, 85, 86, 87, 88, 89, 90, 91, 92, 93, 94, 95, 96, 7, 98, or 99 to 100 percent identical to one of SEQ ID NOs: 2, 4, 6, 8, 10 or 12. The encoding nucleic acid(s) can be provided in naked, plasmid, and/or vector form. Suitable plasmids and vectors, including expression vectors will be appreciated by those of ordinary skill in the art and are within the scope of this disclosure. Further, methods, tools, and techniques for producing, amplifying, storing, and otherwise manipulating encoding nucleic acid sequences, plasmids, and vectors, will be appreciated by those of ordinary skill in the art and are within the scope of this disclosure. Methods, tools, and techniques of determining encoding nucleic acid sequences from polypeptide sequences will be appreciated by one of ordinary skill in the art and are within the scope of this disclosure.

The modified gal1 monomers described above can complex to form modified gal1 dimers. The modified gal1 dimers can be homodimers (formed from the same monomers) or can be heterodimers (formed from different monomers).

Two or four of the modified gal1 monomers described above can be crosslinked to each other to form modified gal1 dimers and/or tetramers. In some aspects, two modified gal1 monomers described above having an unmodified C2, C16, C88, C130 and/or combinations thereof can be crosslinked to each other via an unmodified C2, C16, C88, and/or C130 residue to form a modified gal1 dimer. In some aspects, two modified gal1 monomers described above having an unmodified C2, C16, C42, C60, C88, C130 and/or combinations thereof residue or any combination thereof can be crosslinked to each other.

In some aspects, PEGDA or PEGDMal (PEG-Di-Mal) can be used to crosslink two modified gal1 monomers to form the modified gal1 dimers. In these aspects, the acrylate (or Mal) can interact with the thiol group of an unmodified cysteine on the modified gal1 monomers. In some aspects, the unmodified cysteine in the modified gal1 monomer that reacts with the acrylate of the PEGDA or Mal of PEGDMal can be C2 and/or C130. In some aspects, each modified gal1 monomer of the modified gal1 dimer has a C2S, a C16S, and a C88S mutation and an unmodified C130. In these aspects, the thiol group of C130 in each modified gal1 monomer can react with the acrylate of PEGDA or Mal of PEGDMal to crosslink each monomer via C130. In some aspects, the dimer is a homodimer. In some aspects, the dimer is a heterodimer.

In some aspects, four modified gal1 monomers can be crosslinked to form a modified gal1 tetramer. In some aspects, four modified gal1 monomers described above having an unmodified C2, C16, C88, and/or C130 can be crosslinked to each other via an unmodified C2, C16, C88, and/or C130 residue to form a modified gal1 tetramer. In some aspects, PEGTA or PEGTMal (PEG-tetra-Mal) can be used to crosslink four modified gal1 monomers to form the modified gal1 tetramer. In these aspects, the acrylate or Mal can interact with the thiol group of an unmodified cysteine on the modified gal1 monomers. In some aspects, the unmodified cysteine in the modified gal1 monomer that reacts with the acrylate of the PEGTA or Mal of PEGTMal can be C2 and/or C130. In some aspects, each modified gal1 monomer of the modified gal1 tetramer has a C2S, a C16S, and a C88S mutation and an unmodified C130. In these aspects, the thiol group of C130 in each modified gal1 monomer can react with the acrylate of PEGTA or Mal of PEGTMal to crosslink each monomer via C130.

The modified gal1 monomers, dimers, and/or tetramers can be resistant to oxidative environments as compared to wild-type gal1 monomers, dimers, and tetramers.

The modified gal1 monomers, dimers, and/or tetramers can be made using techniques known to those of ordinary skill in the art.

Pharmaceutical Formulations

Also described herein are pharmaceutical formulations that can include an amount of a modified gal1 monomer, dimer, and/or tetramer or a pharmaceutically acceptable salt thereof and a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations that include the a modified gal1 monomer, dimer, and/or tetramer or pharmaceutically acceptable salt thereof can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

The amount of the modified gal1 monomer, dimer, and/or tetramer or pharmaceutically acceptable salt thereof contained in a pharmaceutical formulation can range from about 0.001 micrograms to about 1000 grams and any value or range therein. In some aspects, the amount of the modified gal1 monomer, dimer, and/or tetramer or pharmaceutically acceptable salt thereof can range from about 0.001 micrograms to about 0.01 micrograms and any value or range therein. In other aspects, the amount of the modified gal1 monomer, dimer, and/or tetramer or pharmaceutically acceptable salt thereof can range from about 0.01 micrograms to about 0.1 micrograms and any value or range therein. In further aspects, the modified gal1 monomer, dimer, and/or tetramer or pharmaceutically acceptable salt thereof can range from about 0.1 micrograms to about 1.0 grams and any value or range therein. In yet further aspects, the modified gal1 monomer, dimer, and/or tetramer or pharmaceutically acceptable salt thereof can range from about 1.0 grams to about 10 grams and any value or range therein. In other aspects, the modified gal1 monomer, dimer, and/or tetramer or pharmaceutically acceptable salt thereof can range from about 10 grams to about 100 grams and any value or range therein. In still other aspects, the modified gal1 monomer, dimer, and/or tetramer or pharmaceutically acceptable salt thereof can range from about 100 grams to about 1000 grams and any value or range therein.

The amount of the modified gal1 monomer, dimer, and/or tetramer or pharmaceutically acceptable salt thereof can range from about 0.01 IU to about 1000 IU and any value or range therein. The amount of the modified gal1 monomer, dimer, and/or tetramer or pharmaceutically acceptable salt thereof can range from 0.001 mL to about 1000 mL and any value or range therein. The amount of the modified gal1 monomer, dimer, and/or tetramer or pharmaceutically acceptable salt thereof can range from about 1% w/w to about 99.9% w/w and any value or range therein of the total pharmaceutical formulation. The amount the modified gal1 monomer, dimer, and/or tetramer or pharmaceutically acceptable salt thereof can range from about 1% v/v to about 99.9% v/v and any value or range therein of the total pharmaceutical formulation. The amount of the modified gal1 monomer, dimer, and/or tetramer or pharmaceutically acceptable salt thereof can range from about 1% w/v to about 99.9% w/v and any value or range therein of the total pharmaceutical formulation.

In some embodiments, the pharmaceutical formulations described herein can be in a dosage form. The dosage form can be administered to a subject in need thereof. The subject in need thereof can have an inflammatory disease or a symptom thereof. The inflammatory disease can be a chronic inflammatory disease. The inflammatory disease can be an autoimmune disease.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intraventricular, intraarticular, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. The subject in need thereof can have an inflammatory disease or a symptom thereof. The inflammatory disease can be a chronic inflammatory disease. The inflammatory disease can be an autoimmune disease.

Where appropriate, the dosage forms described herein can be microencapsulated. The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. The subject in need thereof can have an inflammatory disease or a symptom thereof. The inflammatory disease can be a chronic inflammatory disease. The inflammatory disease can be an autoimmune disease.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. The subject in need thereof can have an inflammatory disease or a symptom thereof. The inflammatory disease can be a chronic inflammatory disease. The inflammatory disease can be an autoimmune disease.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example, 2, 3, 4, or 8 times daily, in which 1, 2, or 3 doses are delivered each time. The aerosol formulations can be administered to a subject in need thereof. The subject in need thereof can have an inflammatory disease or a symptom thereof. The inflammatory disease can be a chronic inflammatory disease. The inflammatory disease can be an autoimmune disease.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some aspects, the aerosol formulations are arranged so that each metered dose of aerosol contains a predetermined amount of an active ingredient, such as the one or more of the modified gal1 monomers, dimers, and/or tetramers described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. The subject in need thereof can have an inflammatory disease or a symptom thereof. The inflammatory disease can be a chronic inflammatory disease. The inflammatory disease can be an autoimmune disease.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. The subject in need thereof can have an inflammatory disease or a symptom thereof. The inflammatory disease can be a chronic inflammatory disease. The inflammatory disease can be an autoimmune disease.

For some embodiments, the dosage form contains a predetermined amount of a compound and/or derivative thereof per unit dose. In other embodiments, the predetermined amount of the compound and/or derivative thereof can be an appropriate fraction of the total amount of the modified gal1 monomer, dimer, and/or tetramer to be administered prior to H-FIRE treatment. Such unit doses may therefore be administered once or more than once a day (e.g.

1, 2, 3, 4, 5, 6, or more times per day). Such pharmaceutical formulations may be prepared by any of the methods well known in the art.

Methods of Using the Modified gal1 Monomers, Dimers, Tetramers, and Pharmaceutical Formulations Thereof The modified gal1 monomers, dimers, and/or tetramers and pharmaceutical formulations thereof described herein can be used for the treatment and/or prevention of a disease, disorder, syndrome, or a symptom thereof in a subject. In some embodiments, modified gal1 monomers, dimers, and/or tetramers and pharmaceutical formulations thereof described herein can be used to treat and/or prevent an inflammatory disease or a symptom thereof. The inflammatory disease can be a chronic inflammatory disease. The inflammatory disease can be an autoimmune disease.

An amount of modified gal1 monomers, dimers, and/or tetramers and/or pharmaceutical formulations thereof described herein can be administered to a subject in need thereof one or more times per day, week, month, or year. For example, the modified gal1 monomers, dimers, and/or tetramers and/or pharmaceutical formulations thereof described herein can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further aspects, the modified gal1 monomers, dimers, and/or tetramers and/or pharmaceutical formulations thereof described herein can be administered one or more times per week, such as 1, 2, 3, 4, 5, or 6 times per week. In other aspects, the modified gal1 monomers, dimers, and/or tetramers and/or pharmaceutical formulations thereof described herein can be administered one or more times per month, such as 1 to 5 times per month. In still further embodiments, the modified gal1 monomers, dimers, and/or tetramers and/or pharmaceutical formulations thereof described herein can be administered one or more times per year, such as 1 to 11 times per year.

The modified gal1 monomers, dimers, and/or tetramers and/or pharmaceutical formulations thereof described herein can be co-administered with a secondary agent by any convenient route. The secondary agent can be a separate compound and/or formulation from the modified gal1 monomers, dimers, and/or tetramers and/or pharmaceutical formulations described herein. The secondary agent can be administered simultaneously with the modified gal1 monomers, dimers, and/or tetramers and/or pharmaceutical formulations thereof. The secondary agent can be administered sequentially with the modified gal1 monomers, dimers, and/or tetramers and/or pharmaceutical formulations described herein. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

In aspects where the modified gal1 monomers, dimers, and/or tetramers and/or pharmaceutical formulations thereof described herein are simultaneously co-administered with a secondary agent, the modified gal1 monomers, dimers, and/or tetramers and/or pharmaceutical formulations thereof described herein can be administered to the subject at substantially the same time as the secondary agent. As used in this context "substantially the same time" refers to administration of the modified gal1 monomers, dimers, and/or tetramers and/or pharmaceutical formulations thereof described herein and a secondary agent where the period of time between administration of the modified gal1 monomers, dimers, and/or tetramers and/or pharmaceutical formulations thereof and the secondary agent is between 0 and 10 minutes.

Where the modified gal1 monomers, dimers, and/or tetramers and/or pharmaceutical formulations thereof is/are sequentially co-administered with a secondary agent, the modified gal1 monomers, dimers, and/or tetramers and/or pharmaceutical formulations thereof can be administered first, and followed by administration of the secondary agent after a period of time. Where the modified gal1 monomers, dimers, and/or tetramers and/or pharmaceutical formulations thereof is/are sequentially co-administered with a secondary agent, the secondary agent can be administered first, and followed by administration of the modified gal1 monomers, dimers, and/or tetramers and/or pharmaceutical formulations thereof after a period of time. The period of time between administration of the modified gal1 monomers, dimers, and/or tetramers and/or pharmaceutical formulations thereof and the secondary agent can range from 10 minutes to about 96 hours. In some aspects, the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the modified gal1 monomers, dimers, and/or tetramers and/or pharmaceutical formulations thereof that can be administered are described elsewhere herein. The amount of the secondary agent will vary depending on the secondary agent. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 50% w/v of the total secondary agent composition or pharmaceutical formulation.

The modified gal1 monomers, dimers, and/or tetramers and/or pharmaceutical formulations thereof can be administered to a patient via an injection. Suitable methods of injection include, but are not limited to. intravenous, intraperitoneal, subcutaneous, intramuscular, intradermal, intraosseous, epidural, intracardiac, intraarticular, intracavernous, intrathecal, intravitreal, intracerebral, gingival, subginigival, intranodal, and intracerebroventricular injection. Other suitable methods of administration of the modified gal1 monomers, dimers, and/or tetramers and/or pharmaceutical formulations thereof include, but are not limited to, topical, transdermal, nasal, or oral delivery.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Galectin-1 (Gal-1) is expressed in many tissues, including the fetal-maternal interface, retina, and thymus, is known to act as an extracellular regulator of innate and adaptive immune cells during inflammation and its resolution. For example, Gal-1 induces apoptosis of activated, polarized T helper 1 cells (Th1) and T helper 17 cells (Th17), yet does not induce apoptosis of naïve T cells (T0), T helper 2 cells (Th2), or T regulatory cells (Treg).[1] Gal-1 can also up-regulate T cell secretion of anti-inflammatory cytokines (e.g., IL-10) and Th2-associated cytokines (e.g., IL-4 and -5), while simultaneously down-regulating Th1 related cytokine expression (INF-γ and IL-2)[2,3]. Gal-1 modulates T cell behavior by recognizing lactosamine glycans conjugated to various receptors, including CD2, CD3, CD7, CD43, and CD45.[4-7] Notably, Gal-1 selectivity for inducing Th1 and Th17 cell apoptosis is related to differences in the surface glycosylation profile of these cells after activation when compared to T0, Th2, and Treg cells,[4-8] and it is this specificity of Gal-1 for certain T cell subsets that makes it an attractive candidate to treat autoimmune and chronic inflammatory conditions mediated by Th1 and Th17 cell dysfunction. Although Gal-1 immune modulating properties are canonically associated with T cells, Gal-1 is known to modulate innate immune cells as well. For example, Gal-1 up-regulates monocyte arginase activity, while also reducing INFγ-induced monocyte expression of FcγR1 and suppressing major histocompatibility complex II (MHCII) expression, phagocytosis, arachidonic acid release, nitric oxide synthesis, and INFγ production. Further, monocytes cultured in the presence of Gal-1 differentiate into tolerogenic dendritic cells (DCs) that produce IL-10 and induce antigen-specific tolerogenic T cell responses.[3] Finally, Gal-1 can enhance DC migration through extracellular matrices,[9] and can mediate selective exit of tolerogenic DCs from peripheral tissue sites to lymph nodes.[10] In agreement with these in vitro observations, Gal-1 is effective for preventing or treating inflammatory and autoimmune pathologies in preclinical animal models of Crohn's disease, multiple sclerosis, myasthenia gravis, rheumatoid arthritis, graft vs host disease, autoimmune uveitis, and T-cell mediated hepatitis.[11-18]

Despite many preclinical successes, Gal-1 translation remains hindered by its biochemical properties. First, Gal-1 activity is attributed to its self-association into a homodimeric quaternary structure that can noncovalently cross-link cell surface glycoproteins into lattices. Thus, for Gal-1 to be active as an immunotherapeutic, its local concentration must exceed the monomer-dimer dissociation constant of approximately 1-7 microM.[19,20] Previous studies have created stable Gal-1 dimers via fusion to an immunoglobulin Fc domain, polypeptide linkers, or leucine zippers.[21-24] However, fusion proteins containing an immunoglobulin Fc domain may bind to Fcγ receptors, resulting in clearance by the reticuloendothelial system or unwanted immune activation.[25] Polypeptide linkers used include the flexible linker domains of tandem-repeat galectins (e.g., galectin-8 and -9), which are susceptible to proteolytic degradation that cleaves the dimer.[26] Leucine zippers derived from nonhuman proteins may be immuno-genic, especially for therapeutics administered repeatedly to sites of ongoing inflammation.[27]

A second biochemical property of Gal-1 that hinders its translation is its susceptibility to inactivation in oxidative environments. Gal-1 is classified as an "S-type lectin" due to an abundance of thiol groups from cysteine residues.[28] In total, Gal-1 has six cysteine residues (C2, C16, C42, C60, C88, C130) four of which (C2, C16, C88, C130) are located on the protein surface and are solvent accessible.[29] Surface cysteine residues on Gal-1 are covalently cross-linked into disulfides in oxidative environments.[30-32] This covalent cross-linking results in a multimeric Gal-1 structure that cannot bind glycans or exert lectin-like activity.[33,34] Prolonged increased local concentrations of reactive oxygen species (ROS) are a hallmark of the progression of inflammatory disease.[35] Thus, Gal-1 is likely rapidly inactivated at sites of intended immunomodulatory action. Previous studies demonstrated that mutating cysteine residues in Gal-1 can improve protein stability.[23,36] Likewise, solvent-accessible cysteine residues can be reacted with iodoacetamide or maleimide to prevent disulfide bond formation in oxidative environments.[37]

Engineering a Gal-1 homodimer that is both stable at low concentrations and resistant to oxidative inactivation would likely yield further improvements in therapeutic efficacy. Toward this end, a poly- (ethylene glycol) (PEG)-cross-linked Gal-1 dimer lacking surface cysteine residues was developed and characterized. Attaching PEG to proteins (i.e., "PEGylation") is a widely used method to improve protein pharmacokinetics and pharmacodynamics because PEG is water-soluble, easy to conjugate onto proteins, biocompatible, and not itself immunogenic except in rare cases.[38] PEG-protein conjugates have been FDA approved for an array of applications spanning from topical products to injectable therapies. However, a review of the literature suggests that an acrylate-thiol dependent PEGylation has not been used to create a stable protein homodimer.[39-41] Here, a poly(ethylene glycol) diacrylate (PEGDA) was used for PEGylation to achieve rapid and selective reaction with cysteine residues on proteins and peptides under mild conditions that are favorable to maintain protein conformation.[42-45] To achieve site-specific PEGylation, 3 of the 4 surface cysteine residues on Gal-1 were mutated to serine residues that are not sensitive to oxidative environments and are not reactive with acrylate ("Tri") (FIGS. 1A-1B). Each acrylate moiety of PEGDA reacts with one cysteine residue on each of two Tri molecules, resulting in the stable, oxidation-resistant Gal-1 homodimer referred to as Tri-PEG-Tri (FIG. 1A).

Results and Discussion

Figure 2E:
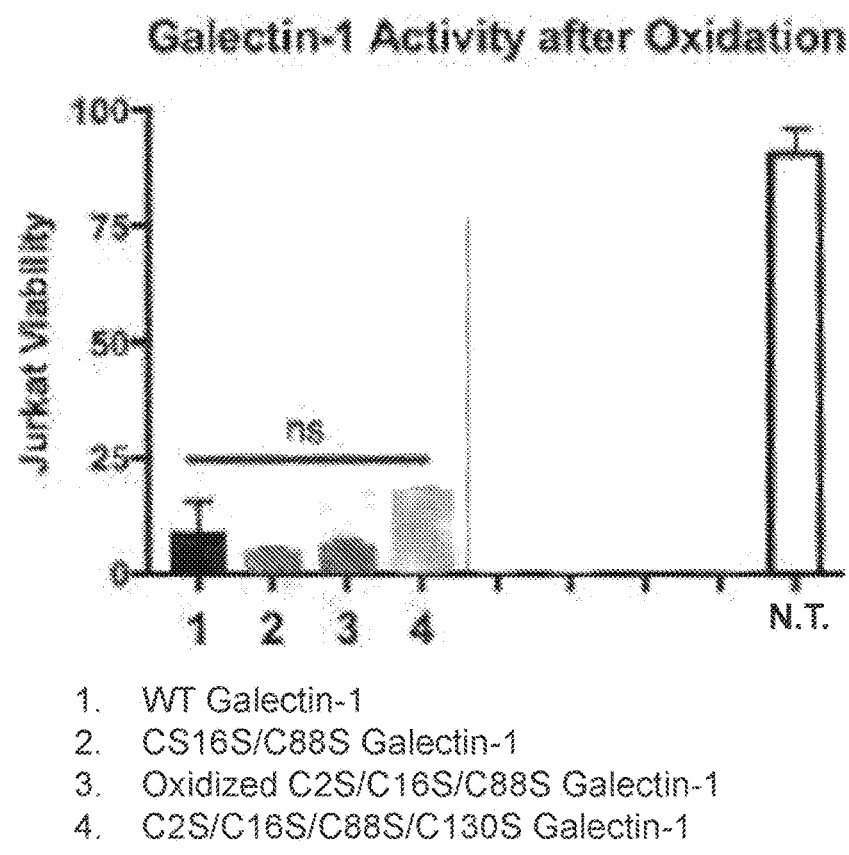
Figure 2F:
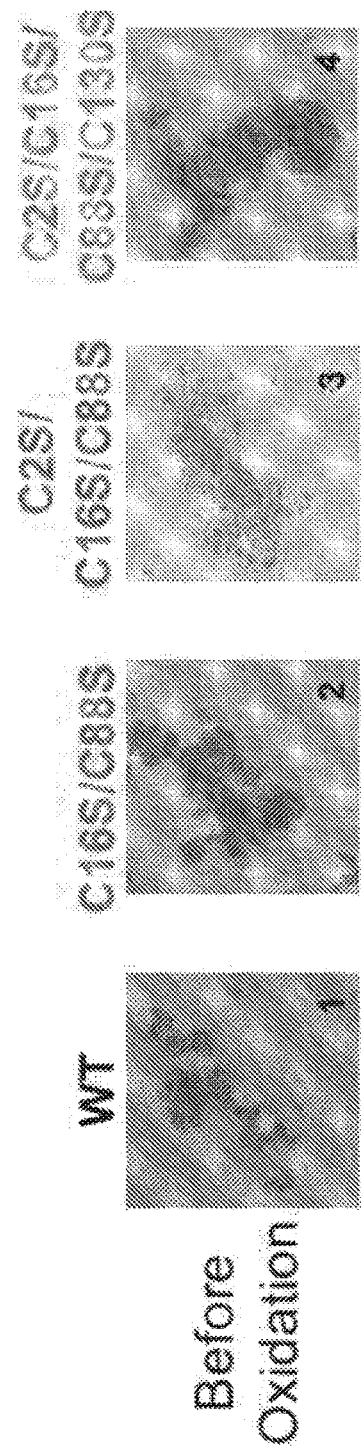

Galectin-1 Mutant Protein Production. FIG. 2A shows a schematic representation of the primary sequence of wild-type Gal-1 and various Gal-1 Cys-to-Ser mutants. "SH" denotes the sulfhydryl groups present on cysteine residues. SH in gray dashed boxes are located within the protein core, while SH in black solid boxes are on the protein surface. To characterize the role of the four surface cysteine residues in Gal-1 carbohydrate recognition and biological activity, residues (C42 and C60) were left unchanged because their proximity to the carbohydrate recognition domain (CRD) suggests they may be important for carbohydrate binding and because they are thought to be solvent inaccessible and therefore not involved in oxidation-induced inactivation (FIG. 2B).[36] All Gal-1 mutants were expressed in *E. coli* and recovered from the soluble fraction in high yield and purity (FIG. 2C). Each mutant Gal-1 demonstrated comparable binding affinity for α-lactose:agarose when compared to wild-type (WT) Gal-1 (FIG. 2D). In contrast to WT Gal-1, all of the mutant proteins could be stored without a reducing agent, such as dithiothreitol (DTT), without the loss of α-lactose:agarose affinity. FIG. 2E shows a graph demonstrating activity of wild-type (WT) Gal-1 and Gal-1 mutants after oxidation. FIG. 2F shows micrographic images of Jurkat T cells treated with WT or various Gal-1 mutants before oxidation, which can demonstrate lectin activity. Together, these data suggested that the CRD of Gal-1 is not altered following mutation of multiple surface-exposed cysteine residues, and that multisite Cysteine-to-Serine Gal-1 mutants are more resistant to oxidation than WT Gal-1.

Figure 3A:
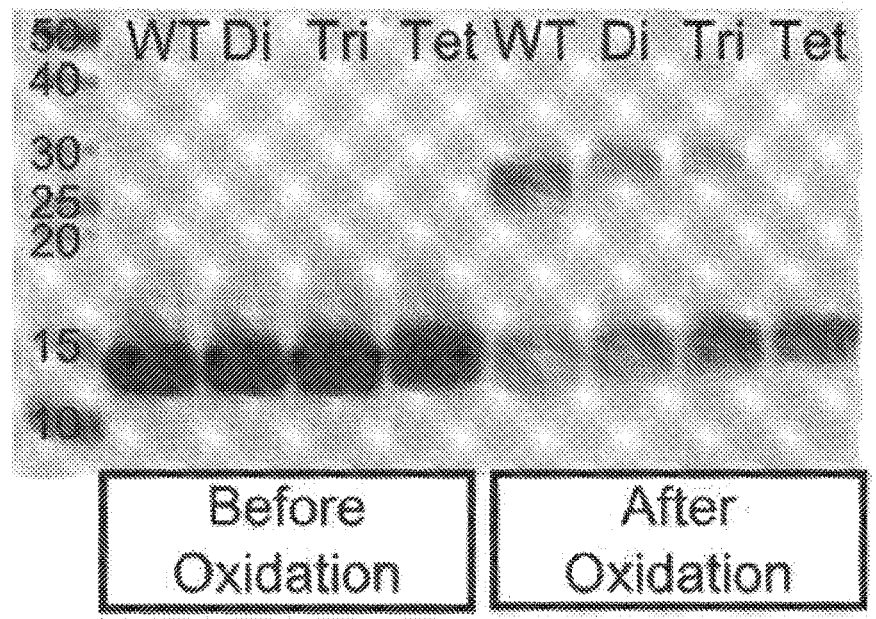
FIGS. 3A-3C can demonstrate that cysteine-to-serine galectin-1 mutants as described herein can be resistant to oxidative inactivation.
Figure 3B:
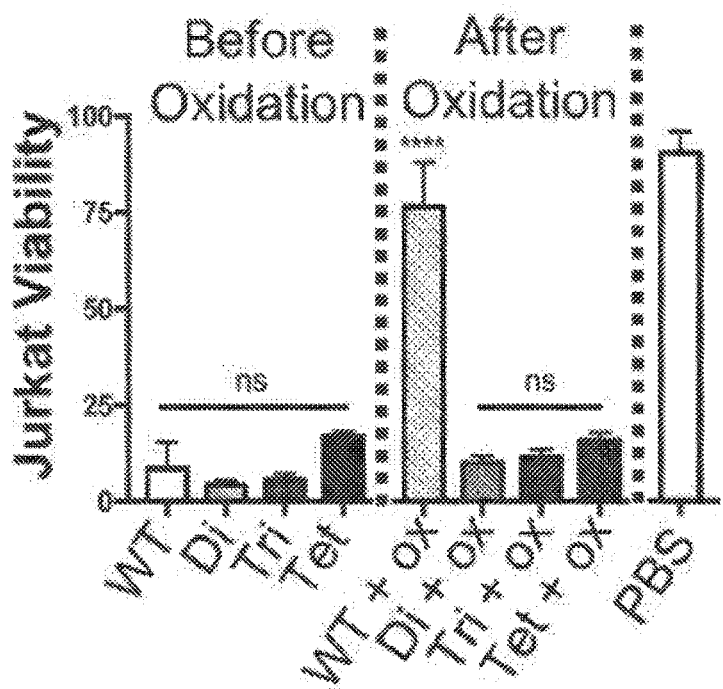
Figure 3C:
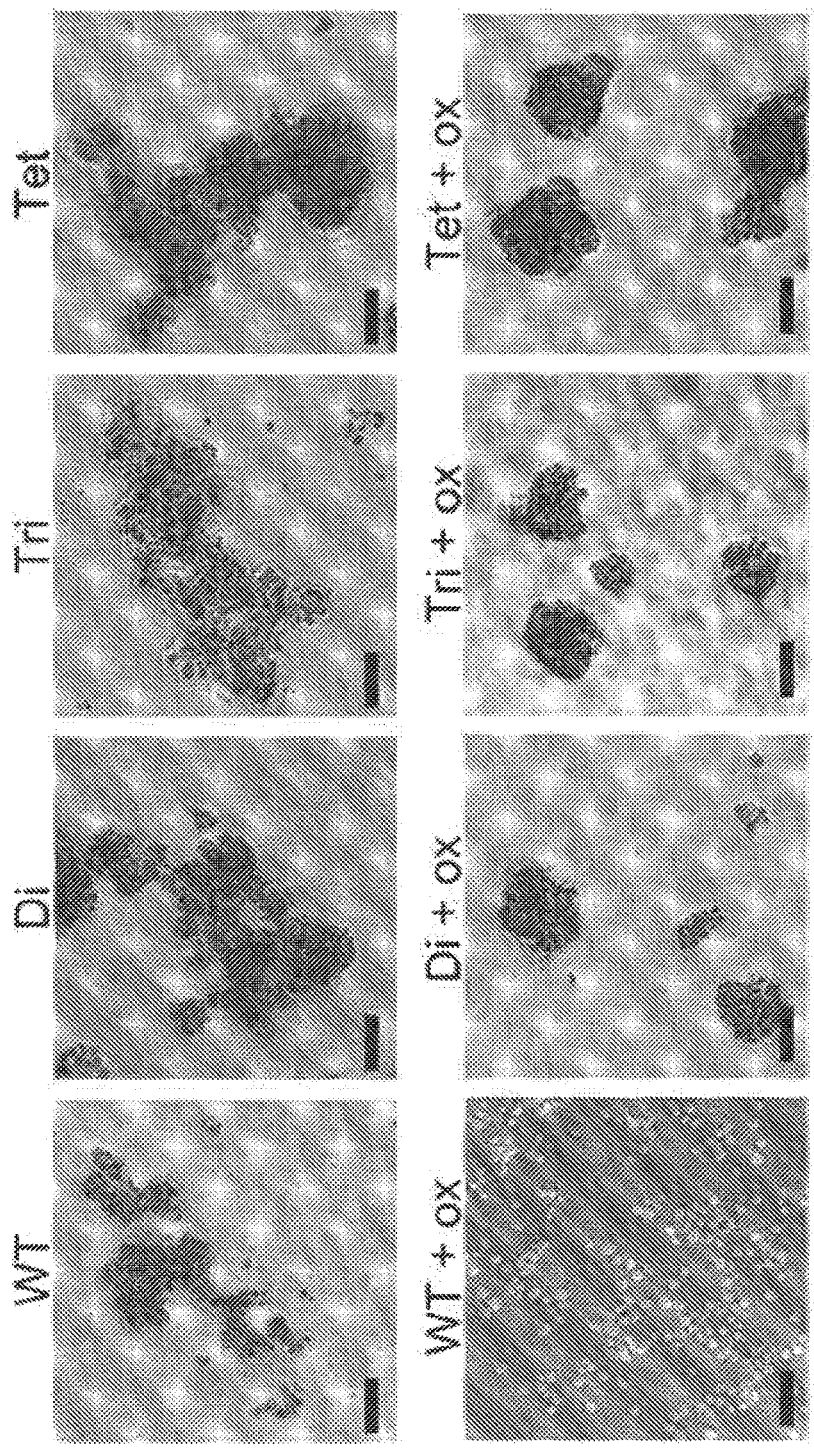

Cysteine to Serine Galectin-1 Mutants are Resistant to Oxidative Inactivation. To compare oxidative inactiva-tion of WT Gal-1 and our Gal-1 mutants, WT, Di, Tri, and Tet Gal-1 were exposed to hydrogen peroxide, a common ROS in inflammation.[46] WT Gal-1 treated with hydrogen peroxide predominantly cross-linked into oligomers (FIG. 3A). In contrast, the oligomer:monomer ratio decreased with the number of surface cysteine residues in Di and Tri Gal-1, as indicated by decreasing intensity of higher molecular weight bands (FIG. 3A). Tet Gal-1 remained monomeric in the presence of ROS (FIG. 3A), consistent with the hypothesis that the two remaining cysteine residues are buried within the core of the protein and not involved in oxidative inactivation. Reduced WT Gal-1 induced agglutination and apoptosis of a human leukemic T cell line, Jurkat T cells (E6-1) (FIGS. 3B-3C), consistent with prior reports.[47] Likewise, all Gal-1 mutants induced rapid Jurkat agglutination and apoptosis (FIGS. 3B-3C). As expected, WT Gal-1 treated with hydrogen peroxide failed to induce T cell agglutination and apoptosis (FIGS. 3B-3C), whereas all Gal-1 mutants treated with hydrogen peroxide induced Jurkat agglutination and apoptosis (FIGS. 3B-3C). We attributed the observed activity of Di and Tri Gal-1 samples treated with hydrogen peroxide to the reduced, monomeric protein fraction detected via gel electrophoresis because all oxidation reactions were performed at Gal-1 concentrations well above the minimum active dose.

Taken together, these results suggest that Gal-1 variants in which multiple surface cysteine residues have been mutated to serine residues retain the pro-apoptotic activity of WT Gal-1 under reducing conditions, yet are also active in oxidative environments. Coupled with our observations that Tet Gal-1 remained monomeric in oxidative environments and without being bound by theory, it is believed that a Gal-1 mutant lacking all surface cysteine residues will demonstrate optimal immunotherapeutic activity at sites of inflammation. Additionally, toward understanding Gal-1 bioactivity through in vitro assays, the stability of Tet Gal-1 in oxidative environments may eliminate the need to use reducing agents that can induce confounding leukocyte apoptosis.[48]

Figure 4A:
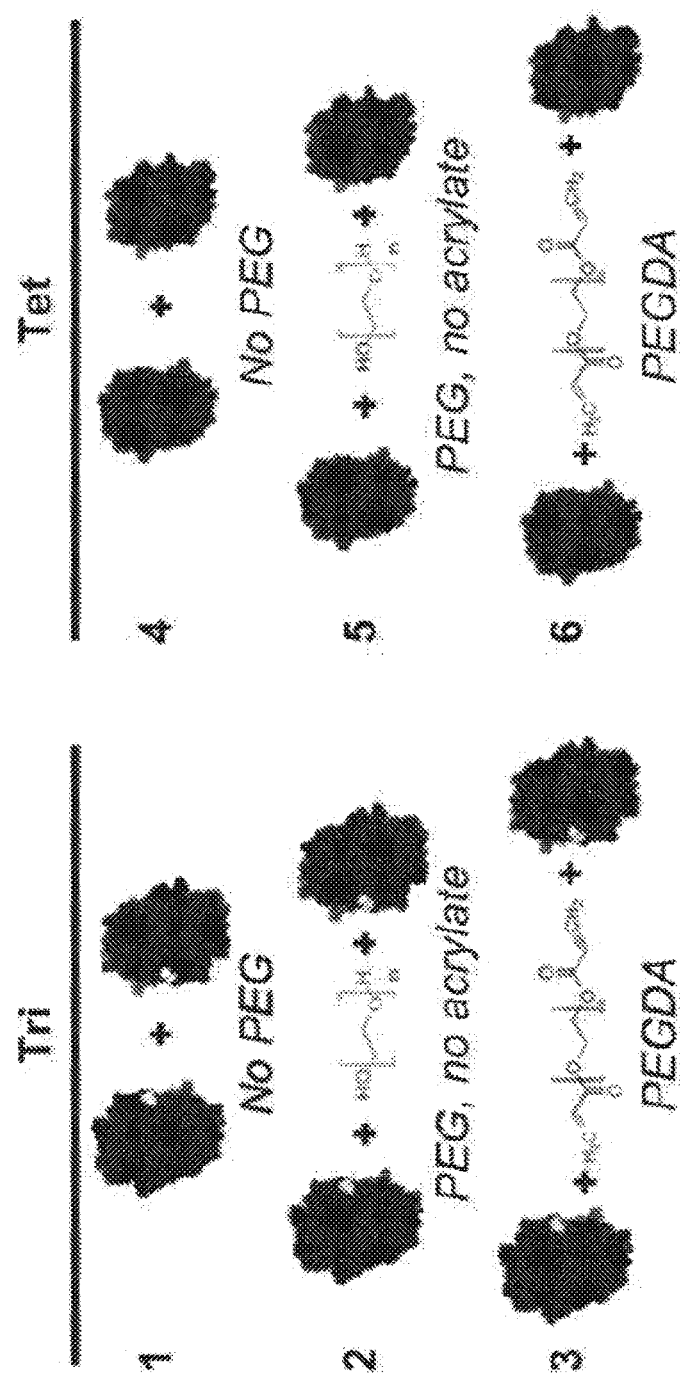
FIGS. 4A-4I can demonstrate that PEGDA cross-links Tri Gal-1 in a cysteine- and acrylate-dependent manner.
Figure 4B:
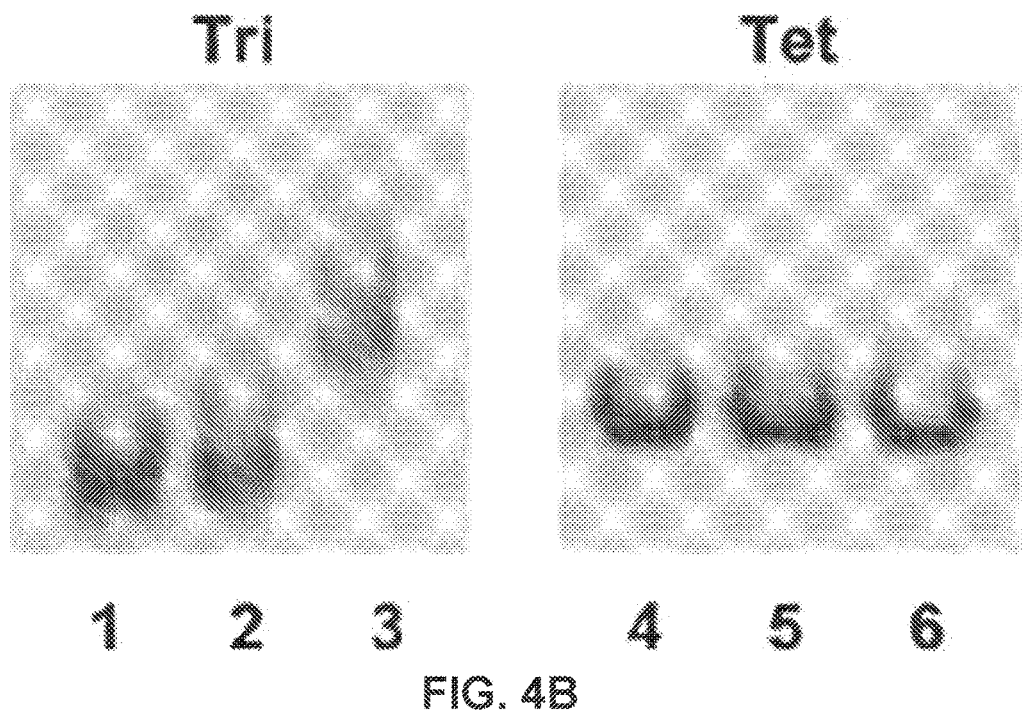
Figure 4C:
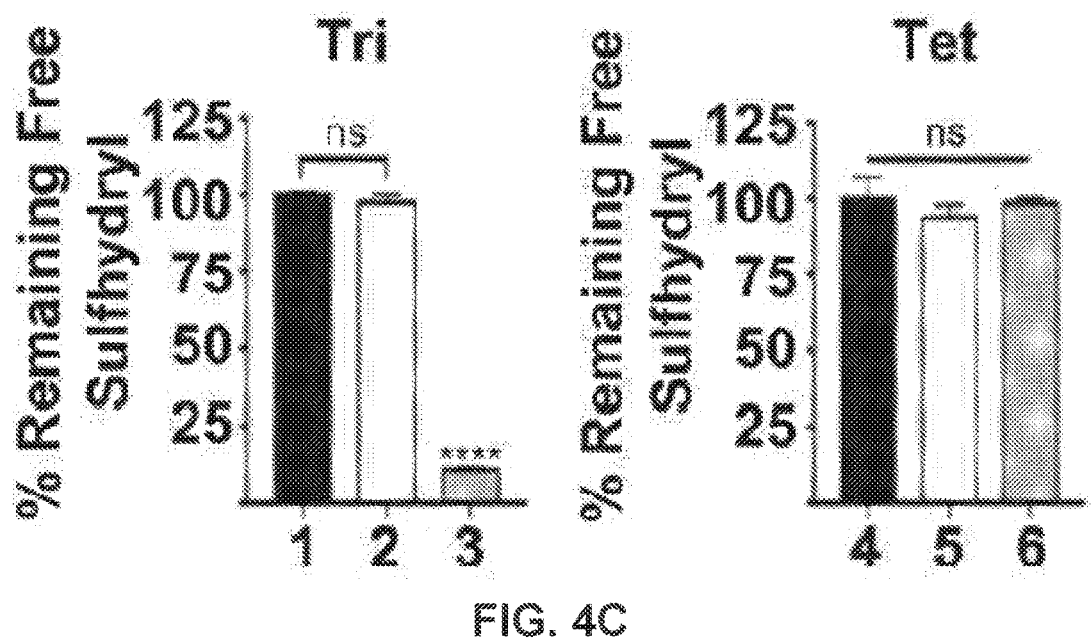

Cross-Linking of Tri Gal-1 via Poly(ethylene glycol) Diacrylate. To stabilize the activity of Cys-to-Ser Gal-1 mutants at low concentrations, we characterized the cross-linking of Tri Gal-1, which has one surface cysteine (C130), via poly(ethylene glycol) diacrylate (PEGDA) (FIG. 1A). First, the reaction of Tri and Tet Gal-1 with PEGDA (Mn=2 kDa) or PEG (Mn=2 kDa) lacking acrylate groups ("PEG") (FIG. 4A) was compared. Tri Gal-1 incubated overnight with a 25-fold excess of PEGDA migrated a shorter distance than Tri Gal-1 alone or Tri Gal-1 incubated with a 25-fold excess of PEG under native gel electrophoresis conditions (FIG. 4B). In contrast, Tet Gal-1 migrated a similar distance alone or after overnight incubation with a 25-fold excess of PEGDA or PEG (FIG. 4B). Likewise, the free thiol content of Tri Gal-1 incubated overnight with a 25-fold excess of PEGDA was significantly lower than that of Tri Gal-1 alone or Tri Gal-1 incubated with a 25-fold excess of PEG, whereas the thiol content of Tet Gal-1 did not change under any conditions (FIG. 4C). FIGS. 4F-4I show graphs demonstrating MALDI-TOF mass spectrometry results. Together, these data demonstrated that PEGDA reacted with Tri, likely through the single surface-exposed cysteine residue C130.

Figure 4D:
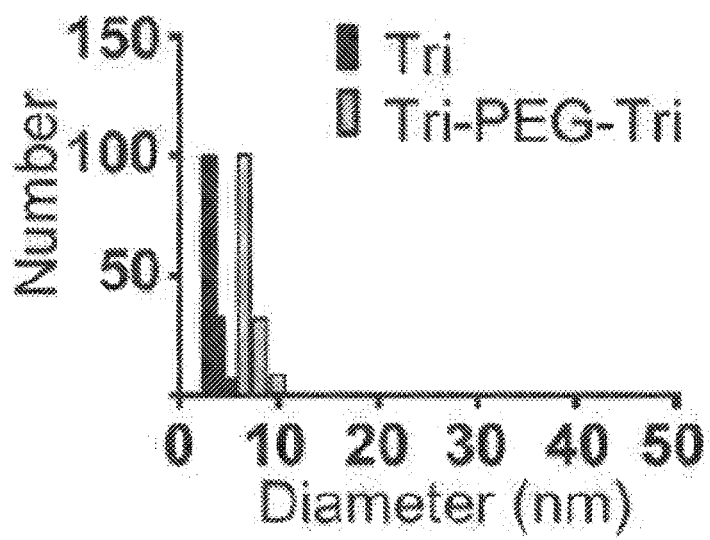

The hydrodynamic diameter of Tri Gal-1 incubated with PEGDA overnight was approximately 2-fold greater than that of Tri Gal-1 alone, as determined via dynamic light scattering (FIG. 4D). These observations suggested that the reaction of PEGDA with Tri Gal-1 did not yield large aggregates. Likewise, the relatively small size and narrow polydispersity suggested that the reaction of PEGDA with Tri Gal-1 did not yield polymers of (PEG-Tri-PEG-Tri)$_n$, which would be expected if more than 1 cysteine residue in Tri Gal-1 was accessible on the surface of the protein. Instead, collectively, these data suggested that PEGDA cross-linked Tri Gal-1 into a dimer via the surface-exposed C130 residue.

Figure 4E:
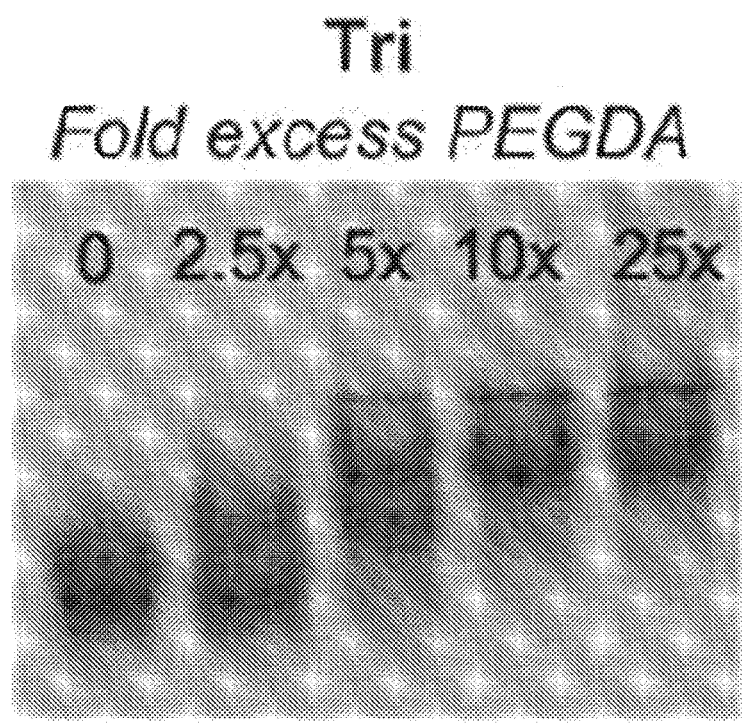
Figure 4F:
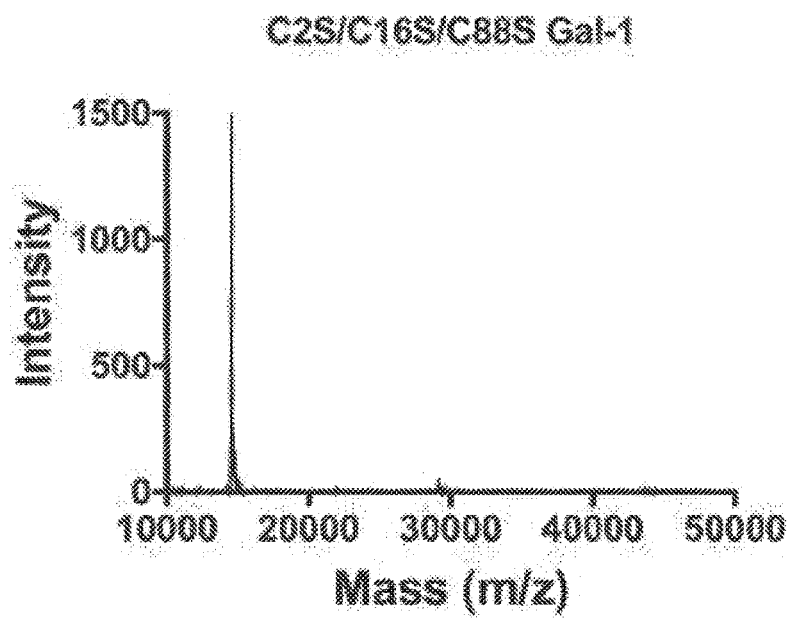
Figure 4G:
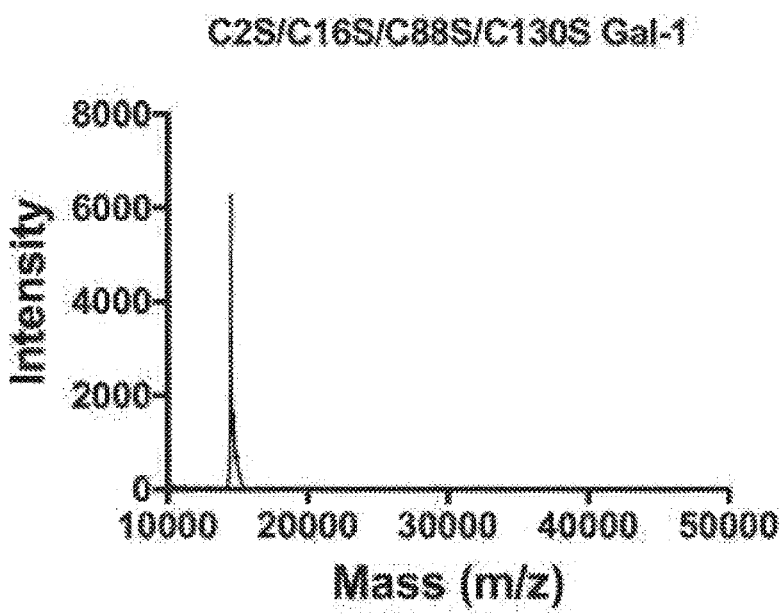
Figure 4H:
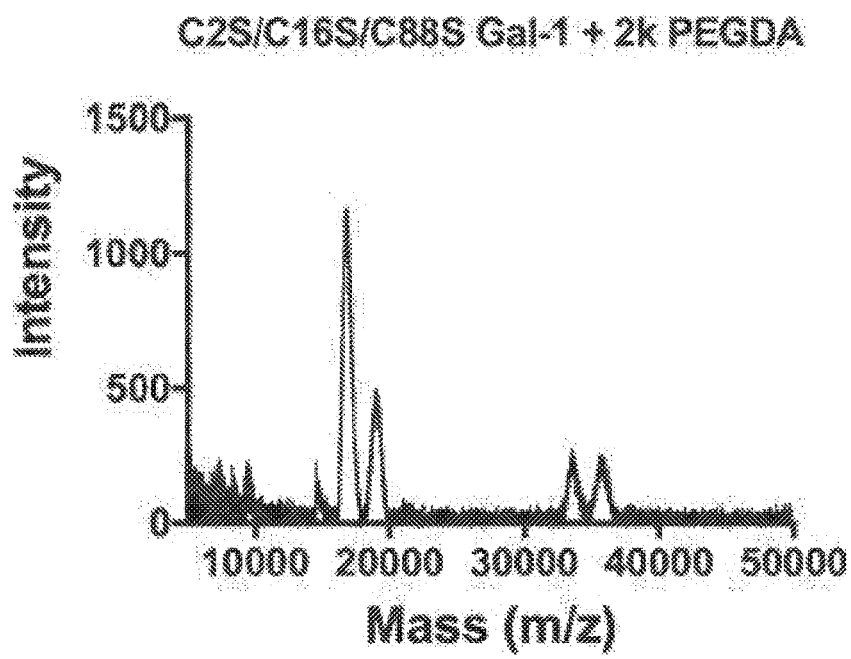
Figure 4I:
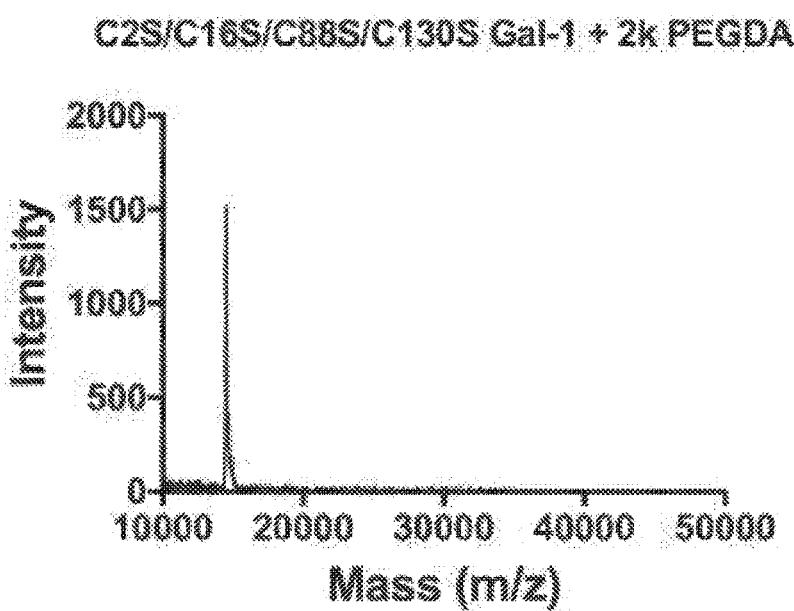
Figure 5A:
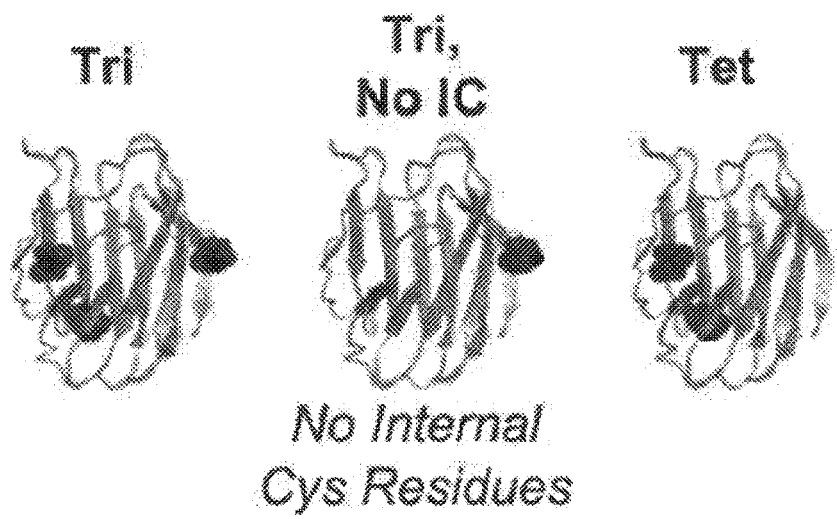
(FIG. 5A) Tri Gal-1, Tri, No IC Gal-1, and Tet Gal-1 crystal structures with cysteine residues highlighted in black.
Figure 5B:
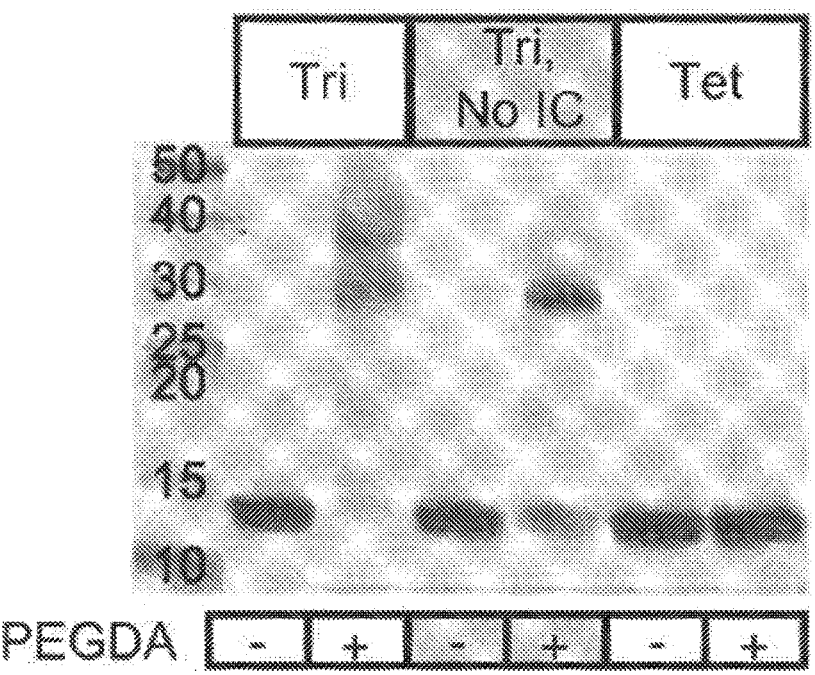
(FIG. 5B) Scan of SDS-PAGE gel of Tri Gal-1, Tri, No IC Gal-1, and Tet Gal-1 after overnight incubation alone or with 25-fold excess PEGDA.
Figure 7:
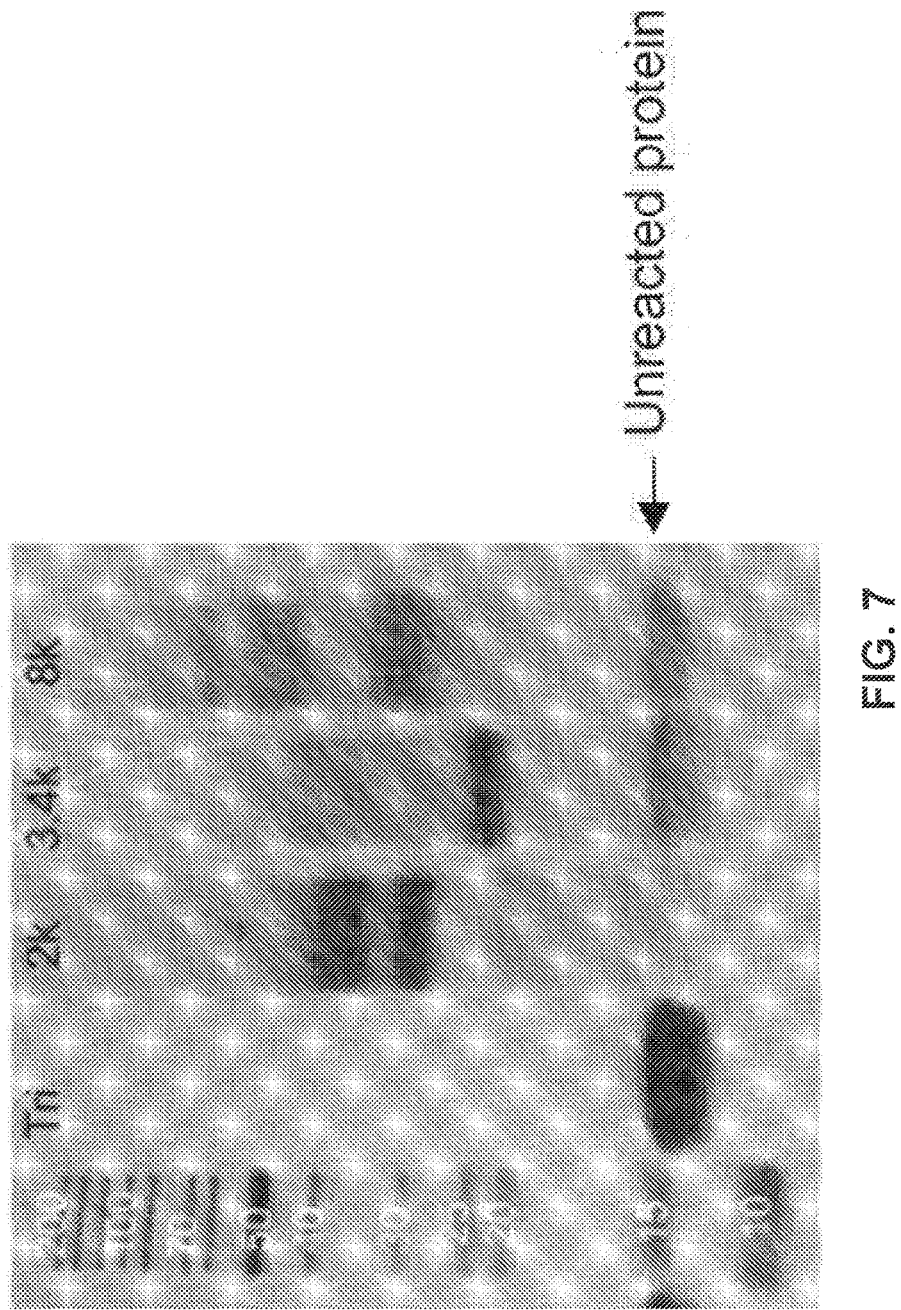
FIG. 7 shows a scan of SDS PAGE gel of Tri Gal-1+25x excess PEGDA at various molecular weights.
Figure 8A:
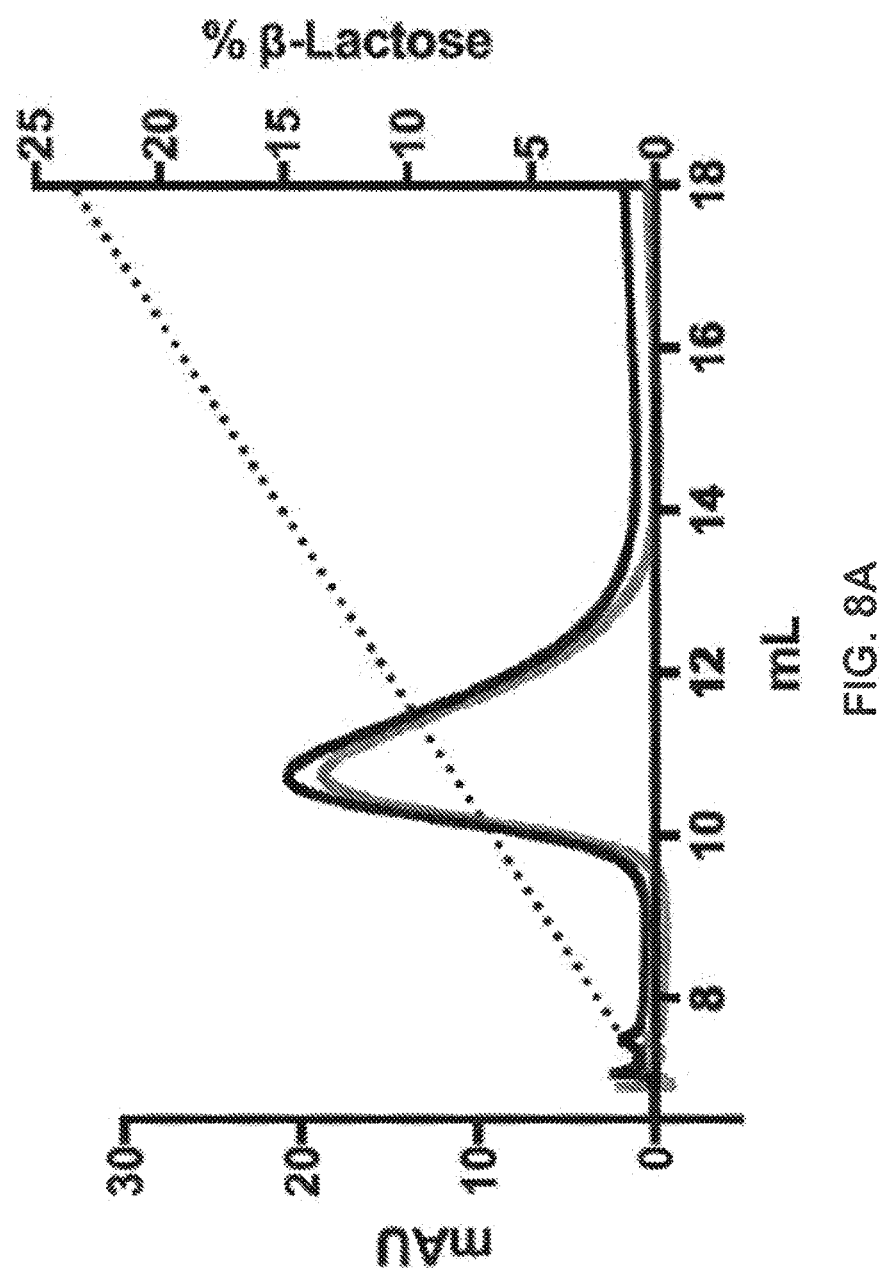
FIGS. 8A and 8B show graphs that can demonstrate traces of protein elution from α-lactose:Agarose resin using a gradient of β-Lactose.
Figure 8B:
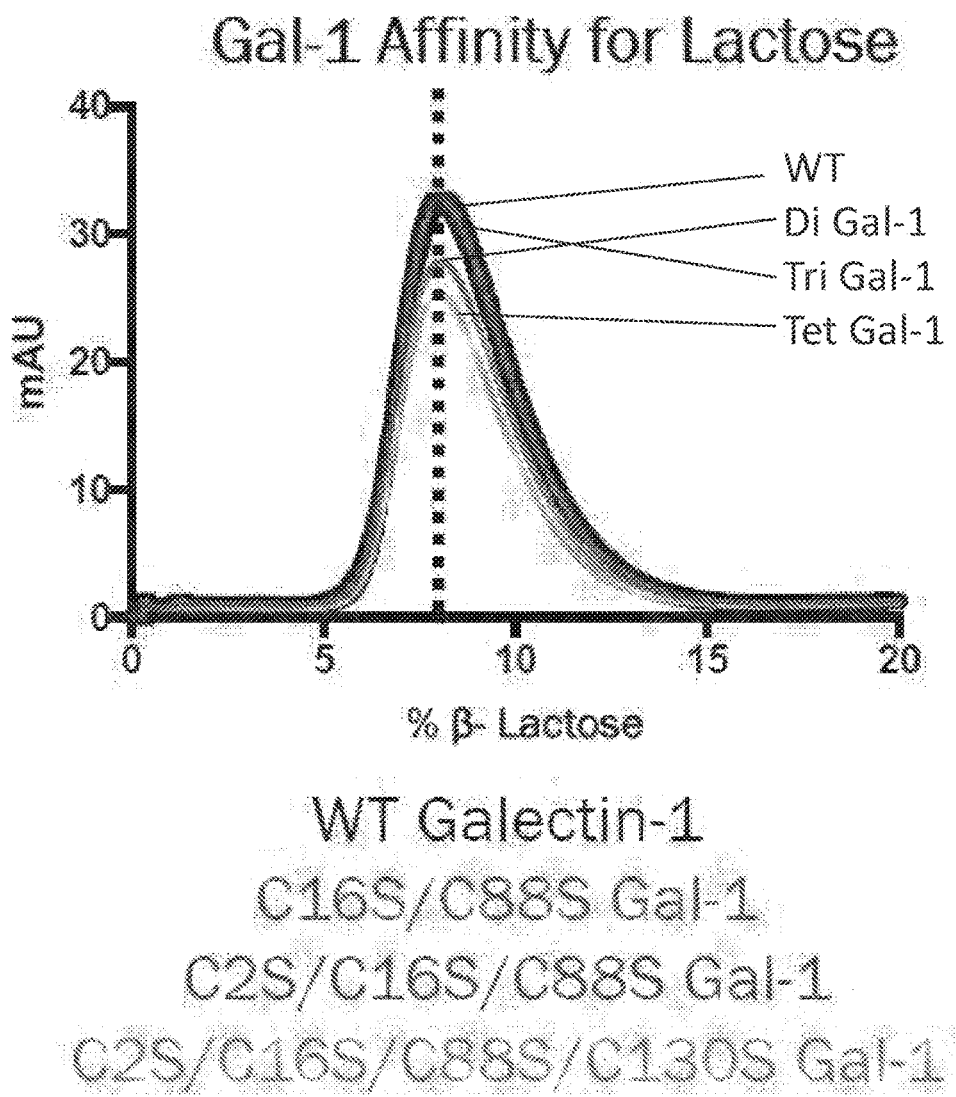

Finally, to identify reaction conditions that favored Tri Gal-1 cross-linking via PEGDA, we evaluated the extent of reaction of Tri Gal-1 incubated overnight with different molar excesses of PEGDA or different molecular weight PEGDAs. Two kDa PEGDA was used in all subsequent studies because it reacted most efficiently with Tri Gal-1 (FIG. 7). Under all conditions tested, a fraction of Tri Gal-1 incubated with PEGDA migrated a shorter distance via native PAGE (FIG. 4E). However, at a molar excess of PEGDA less than 10-fold, native PAGE identified unreacted or incompletely reacted Tri Gal-1. As the PEGDA molar excess was increased, the native PAGE band compressed into a single band indicative of a single higher molecular weight species. Importantly, this observation further supported the conclusion that PEGDA reacted with C130 to cross-link Tri Gal-1 into a dimer, since reactions between PEGDA and multiple cysteine residues (e.g., those in the core of the protein) would be expected to yield oligomers or aggregates that would appear as a broader band or smear on the native PAGE gel. For all subsequent studies, Gal 1 mutants were reacted with a 25-fold molar excess of PEGDA. We further characterized the reaction between PEGDA and C130 on the surface of Gal-1 using Tri Gal-1, a mutant of Tri Gal-1 lacking the internal cysteine residues ("Tri, No IC"), and Tet (FIG. 5A). Tri Gal-1 and Tri, No IC Gal-1 incubated overnight with a 25-fold molar excess of PEGDA migrated a shorter distance than Tri Gal-1 alone or Tri, No IC Gal-1 under denaturing conditions (FIG. 5B). The second band in the lane of Tri Gal-1 plus PEGDA can be attributed to to residual PEGDA remaining after buffer exchange, which reacted with internal cysteine residues that were exposed when Tri Gal-1 was denatured. Unexpectedly, more unreacted Gal-1 was detected in lanes for Tri, No IC Gal-1 incubated with PEGDA when compared to Tri Gal-1, which could be due to subtle changes in the accessibility of C130 on Gal-1 variants with or without internal cysteine residues. However, both Tri Gal-1 and Tri, No IC Gal-1 bound α-lactose:agarose with comparable affinity, suggesting that overall protein structure was unchanged (FIG. 8A). FIGS. 8A and 8B show graphs that can demonstrate traces of protein elution from α-lactose:Agarose resin using a gradient of β-Lactose. In FIG. 8A, grey line is Tet Gal-1 and the Black line is Tri, No Internal Cysteines Gal-1, dotted line is the % β-Lactose over elution volume. The dotted line in FIG. 8B is the peak % β-Lactose. In contrast, Tet Gal-1 migrated a similar distance alone or after overnight incubation with a 25-fold excess of PEGDA (FIG. 5B). Likewise, the free thiol content of Tri Gal-1 or Tri, No IC Gal-1 incubated overnight with a 25-fold excess of PEGDA was significantly lower than that of Tri Gal-1 or Tri, No IC Gal-1 alone, whereas the thiol content of Tet Gal-1 did not change (FIG. 5C). Together these data suggested that PEGDA selectively reacted with C130 on the surface of Gal-1, whereas cysteine residues located within the core of the protein were inaccessible and unreactive.

Finally, because the ε-amine of lysine can react with acrylate under some conditions,[49] we also quantified the primary amine content of Tri Gal-1, Tri, No IC Gal-1, and Tet Gal-1 using the fluoraldehyde o-phthaldialdehyde (OPA) fluorescence assay. The primary amine content of all proteins after overnight reaction with a 25-fold excess of PEGDA was similar to each protein alone (FIG. 5D), demonstrating that PEGDA does not react with Gal-1 lysine residues under the conditions used in this report.

Taken together, these data can demonstrate that PEGDA can be used to cross-link Tri Gal-1 into Tri-PEG-Tri homodimers under mild aqueous conditions, and that both surface cysteine residues and acrylate moieties are required for PEGDA conjugation to Gal-1.

Figure 6A:
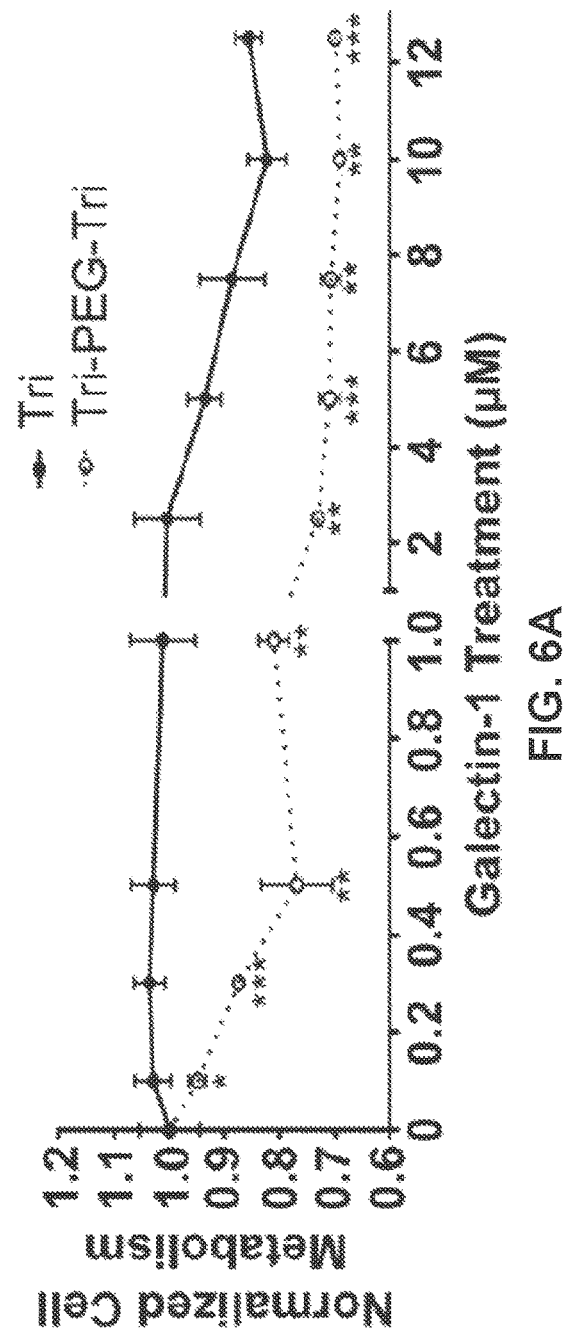
FIGS. 6A-6E can demonstrate that can Tri-PEG-Tri has a lower effective dose than Tri Gal-1.
Figure 6C:
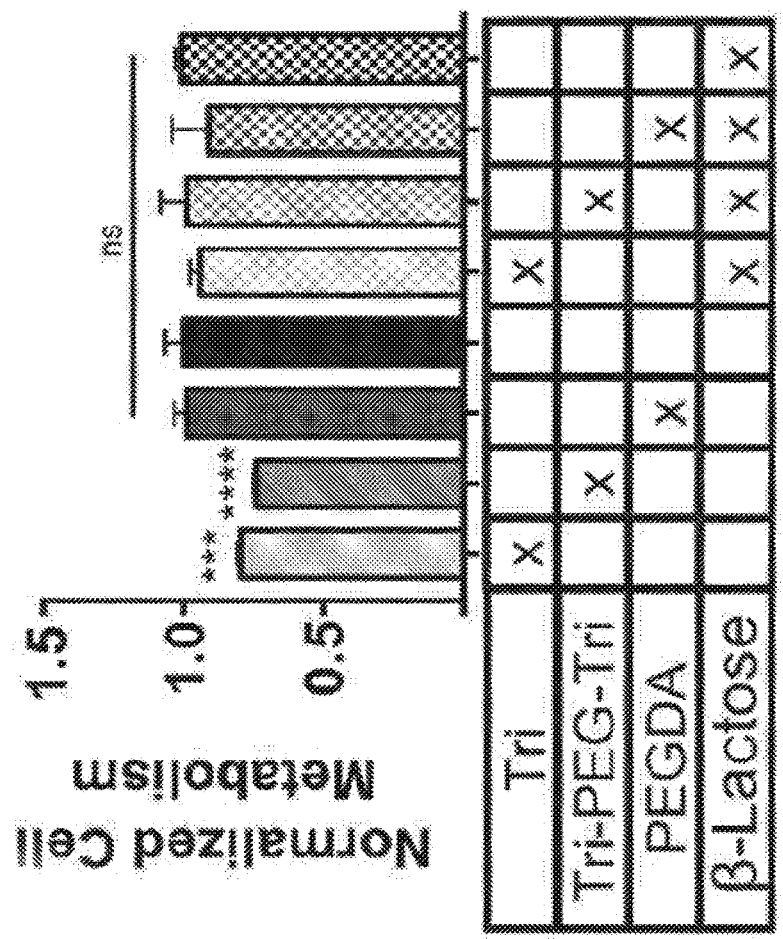
Figure 6B:
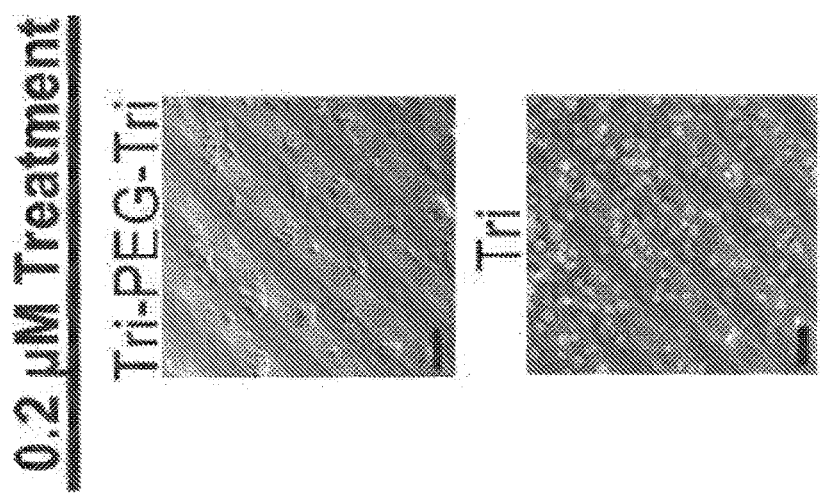
Figure 6D:
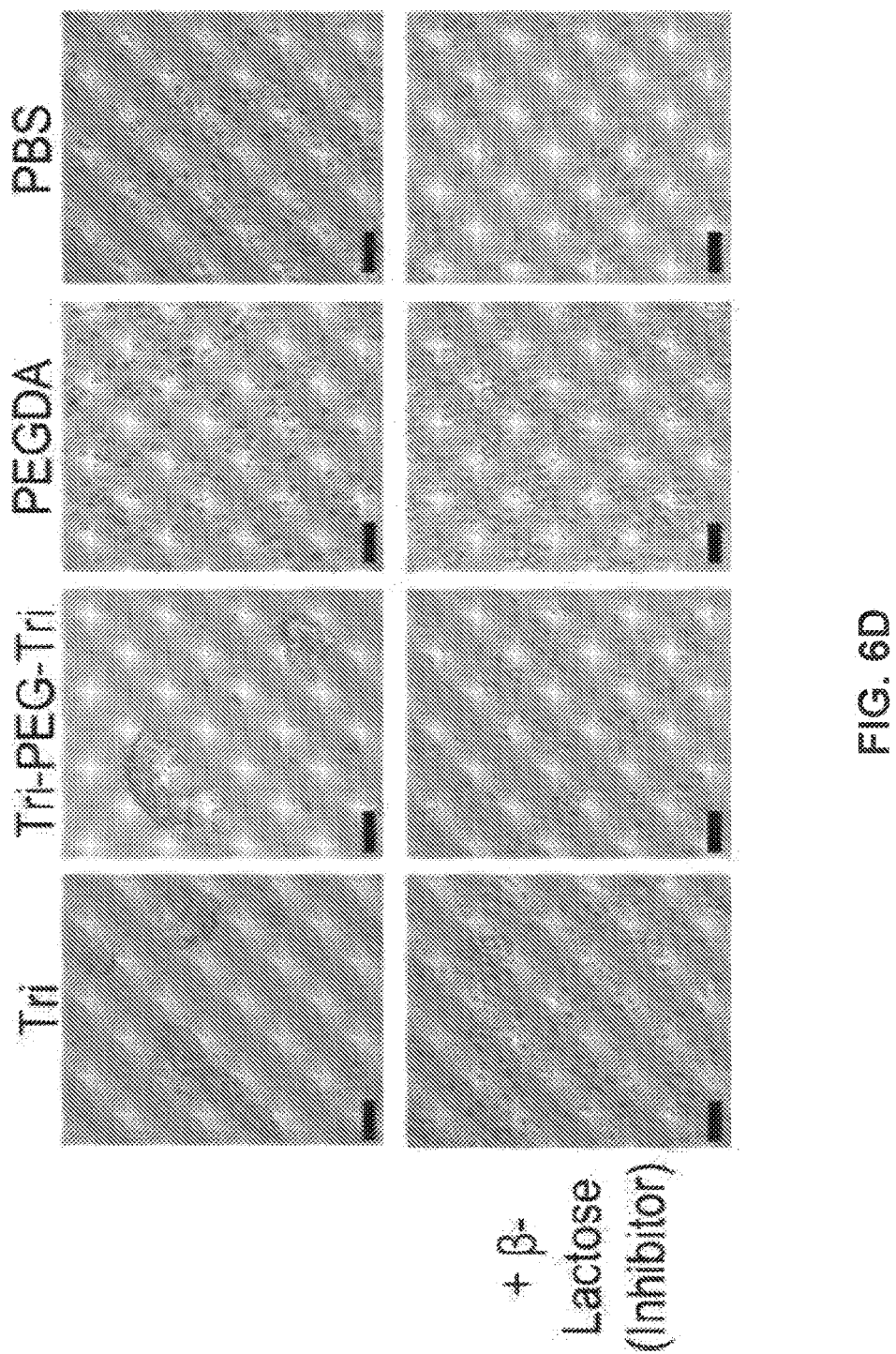
Figure 6E:
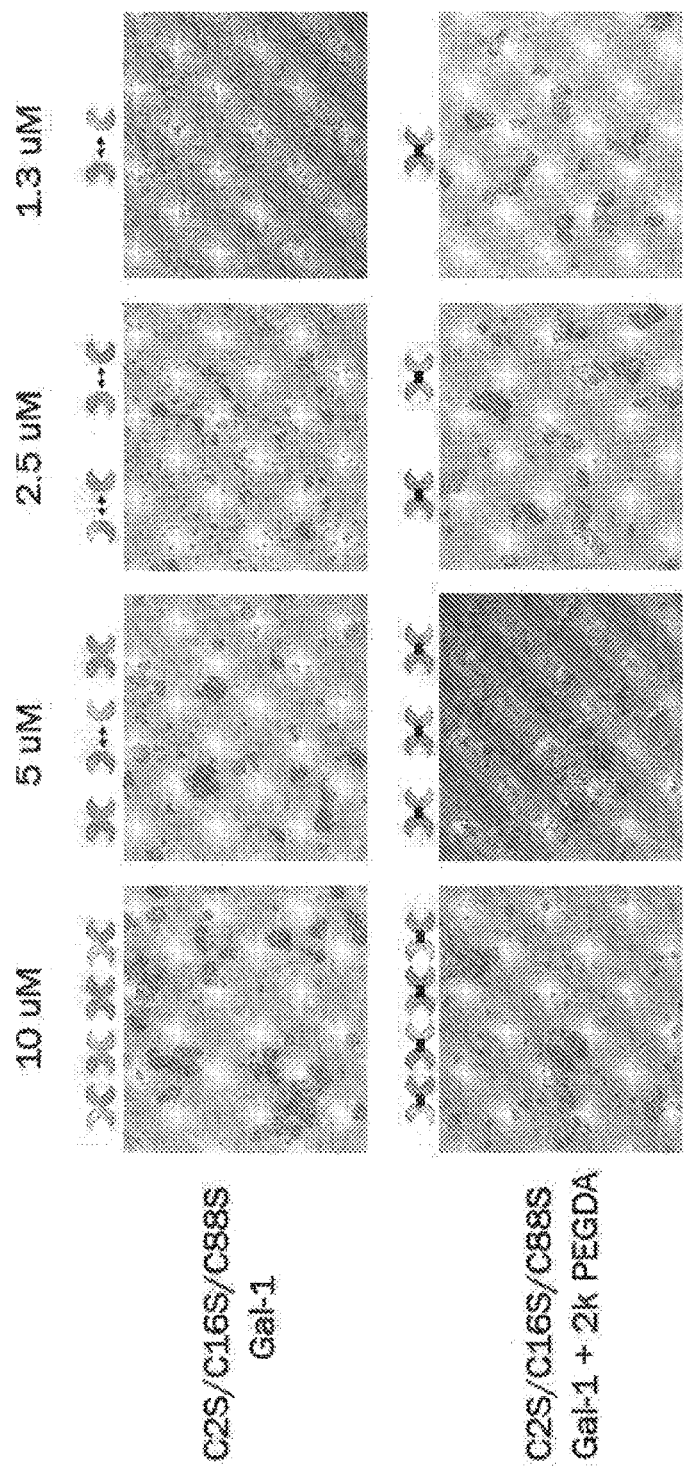

Tri-PEG-Tri is More Active Than Tri Gal-1 at Low Concentrations. The biological activity of Tri-PEG-Tri and Tri Gal-1 ws compared via Jurkat T cell agglutination and metabolic activity (FIGS. 6A-6D). 0.1 microM Tri-PEG-Tri decreased Jurkat T cell metabolic activity, suggestive of T cell death, to a greater extent than Tri Gal-1, which was inactive at this dose. Tri-PEG-Tri activity reached a maximum at approximately 0.5 microM, which was more than 10-fold lower than the concentration of Tri Gal-1 needed to decrease Jurkat T cell metabolic activity (FIG. 6A). Visibly, 0.2 microM Tri-PEG-Tri induced Jurkat T cell agglutination, an early marker of lectin activity, whereas 0.2 microM Tri Gal-1 failed to induce Jurkat T cell agglutination (FIG. 6B). Importantly, PEGDA alone failed to induce Jurkat T cell agglutination or decrease metabolic activity (FIGS. 6C and 6D), suggesting that the observed changes in Jurkat T cell behavior were due to the CRD domain of Tri-PEG-Tri. To further confirm the role of the CRD domain of Gal-1, we evaluated Jurkat T cell metabolism in the presence of Tri-PEG-Tri or Tri Gal-1 plus soluble β-lactose, a known Gal-1 inhibitor. Neither Tri-PEG-Tri nor Tri Gal-1 induced Jurkat T cell agglutination or decreased cell metabolism in the presence of soluble β-lactose (FIGS. 6C and 6D), demonstrating that the enhanced activity of Tri-PEG-Tri was mediated by specific recognition of cell surface glycans via the CRD of Gal-1, and not by other toxicities or nonspecific interactions. FIG. 6E shows microscopic images of Jurkat T cells treated with various concentrations of Tri Gal-1 mutants with and without PEGDA.

Summary

Use of Gal-1 as an immunotherapeutic is hindered by its unstable dimeric conformation and rapid inactivation in oxidative environments, which together necessitate highly concentrated and repeated dosages to be effective. Engineering Gal-1 to be resistant to oxidative inactivation and to maintain a stable dimer conformation at lower concentrations can improve its therapeutic potential. Here it can be demonstrated that Gal-1 mutants in which surface cysteine residues were replaced with serine residues retained the carbohydrate-binding proper-ties and lectin activity of the wild-type protein. Unlike the wild-type protein, however, these mutants are also active in oxidative environments, such as those frequently associated with chronic inflammation or other autoimmune conditions. A Gal-1 mutant having a single surface cysteine residue was cross-linked into a homodimer via a mild Michael-type addition reaction with PEGDA. This stabilized dimeric construct of Gal-1 had a minimum effective dose that was more than an order of magnitude lower than both WT Gal-1 and oxidation-resistant mutants. The enhanced activity and resistance to oxidative inactivation of Tri-PEG-Tri will can result in lower and less frequent dosing regimens to achieve therapeutic efficacy, thereby addressing long-standing challenges in translation of Gal-1 as an immunotherapeutic drug.

Materials and Methods

Cloning and Mutagenesis of C16S/C88S Galectin-1 "Di", C2S/C16S/C88S Galectin-1 "Tri", C2S/C16S/C88S/C130S Galectin-1 "Tet", and C2S/C16S/C42S/C60S/C88S "Tri, No IC". A gene encoding recombinant human galectin-1 was obtained from Origene. Cysteine to Serine mutations were made using the QuikChange Multisite Mutagenesis kit (Agilent). The following primers were used: C2S: 5'-gagatac-catggctagtggtctggtcgccag-3', 5'-ctggcgaccagaccactagc-cat-ggtatatctc-3', C16S: 5'-ctcaaacctggagagagccttcgagtgcgag-3', 5'-ctcgcactcgaaggctctctccaggtttgag-3', C42S: 5'-ggttgaa gtgcag-gctcaggttgttgctgtc-3, 5'-gacagcaacaacctgagcctgcactt-caacc-3', C60S: 5'-gccaacaccatcgtgagcaacagcaaggacg-3, 5'-cgtccttgctgtt-gctcacgatggtgttggc-3', C88S: 5'-agtgttgca gaggtgagcatcaccttcg-acc-3', 5'-ggtcgaaggtgatgctcacctc tgcaacact-3', and C130S: 5'-tcaaaggccacactttgatcttgaagt-caccgtca-3', 5'-tgacggtgacttcaagatc-aaaagtgtggcctttga-3'. Mutagenesis was completed according to manufacturer's instructions. Positive clones were sampled and used to inoculate 5 mL 100 microg/mL ampicillin-containing LB broth. Cultures were grown overnight at 37° C., 220 rpm on an orbital shaker. Plasmids were isolated from cultures via a plasmid mini-prep kit (Qiagen), according to manufacturer's instructions, and sequenced at the Interdisciplinary Center for Biotechnology Research at the University of Florida or GeneWiz.

Protein Expression and Purification. Methods were based off of previous work. 50 Origami B (DE3) *E. coli* (Novagen) were transformed with pET-21d-Galectin-1, pET-21d-C16S/C88S Galectin-1, pET-21d-C2S/C16S/C88S Galectin-1, pET-21d-C2S/C16S/C42S/C60S/C88S, or pET-21d-C2S/C16S/C88S/C130S Galectin-1 vectors and selected on 100 microg/mL ampicillin- and 50 microg/mL kanamycin A-doped LB/agar plates overnight at 37° C. Positive clones were selected to inoculate 5 mL 100 microg/mL ampicillin- and 50 microg/mL kanamycin A-containing LB broth. Cultures were grown overnight at 37° C., 220 rpm on an orbital shaker. Cultures of positive clones were then subcultured into 1 L 100 microg/mL ampicillin- and 50 microg/mL kanamycin A-containing 2×TY broth (10 g/L Yeast, 16 g/L Tryptone, and 5 g/L NaCl) and grown at 37° C., 225 rpm on an orbital shaker until an optical density of 0.6-0.8 (λ=600 nm) was reached. Protein expression was induced with 0.5 milliM isopropyl β-D-1-thiogalactopyranoside (IPTG) and incubated for 18 h at 18° C., 225 rpm in an orbital shaker. Bacteria were pelleted by centrifugation, and washed with phosphate buffered saline (PBS). Bacteria were lysed with B-PER (Thermo Fisher), a protease inhibitor tablet (Thermo Fisher), 300 units DNase I from bovine pancreas (Sigma), and 100 micorg lysozyme (Sigma) for 20 min. Lysed bacteria was cleared by centrifugation, and supernatant containing recombinant proteins was loaded onto columns containing α-lactose:Agarose (Thermo Fisher) equilibrated with PBS. Columns were washed with 20-30 column volumes of PBS and bound galectin was eluted with 100 milliM β-lactose in PBS. β-Lactose was removed by centrifugation using Amicon filter tubes (MWCO 10 kDa) (Millipore). Protein molecular weight and purity were analyzed with SDS-PAGE. Protein concentrations were determined using the 660 nm assay (Thermo Fisher) calibrated with bovine serum albumin. Wild-type Galectin-1 was purified and stored in 8 milliM DTT. All mutated variants of Galectin-1 were purified and stored in PBS without DTT.

Binding Affinity of Di, Tri, Tri, No IC, and Tet. Lactose-binding affinity of WT Gal-1 and Gal-1 mutants was determined using affinity chromatography on an AKTA Pure chromatography system (GE Life Sciences) equipped with an α-lactose:agarose column (Sigma-Aldrich). Proteins were eluted with a linear gradient of β-lactose (Sigma-Aldrich) in PBS. Proteins were detected via absorbance at 280 nm. Binding affinity experiments were repeated in triplicate and representative traces were plotted.

Galectin-1 Oxidation Studies. Studies were conducted according to methods reported previously by Guardia et al. 29 Galectin-1 and all mutated variants were exposed to 167 mM hydrogen peroxide for 30 min at room temperature, followed by 167 U/mL catalase for 15 min to inactivate hydrogen peroxide. An aliquot of each sample was diluted in Laemmli Sample Buffer (Bio-Rad) in the absence of 2-Mercaptoethanol (βME) and analyzed via SDS-PAGE on precast "Any kD gels" (Bio-Rad) at 150 V for 50 min, followed by Coomassie Blue staining. The remaining sample was used in Jurkat T cell apoptosis studies. 5 microM wild-type Gal-1 or mutated variants was added to 20,000 Jurkat T cells/well (Cells from ATCC, generous gift from Dr. Benjamin Keselowsky) in complete media (RPMI 140 supplemented with 10% Fetal Bovine Serum (FBS) (Hyclone), 1% penicillin-streptomycin (Gibco), L-glutamine 200 mM (HyClone), 1% HEPES buffer (Hyclone)) and incubated for 18 h at 37° C., 5% CO2. Jurkat T cells were imaged with light microscopy after 18 h to assess agglutination. To assess viability, cells were stained with 7-AAD and run on BD FACS Canto flow cytometer. FCS Express (BD Biosciences) was used to analyze the data. Using untreated cells as a control population, cells were gated and viability was assessed based on fluorescence intensity.

PEGylation of Galectin-1. PEGDA (Mn ~2000, Sigma) (Mn ~3400, 8000, Alpha Alfesar) or PEG (Mn about 2000, Fisher) was added to Tri, Tri, No IC, and Tet in 1×PBS (pH 7.4) at a 0- to 25-fold molar excess. These solutions were incubated under stirring conditions overnight at room temperature. Unreacted PEGDA was separated from the sample using Amicon filter tubes (MWCO 10 kDa) (Millipore). Molecular weight and purity were analyzed with SDS-PAGE, native PAGE, and dynamic light scattering (Brookhaven). Dynamic light scattering was measured on a Brookhaven 90Plus Particle Size Analyzer (Brookhaven Instruments Inc., NY) and analyzed with BIC Particle Sizing Software. Briefly, 30 microM Gal-1 in PBS before and after PEGylation was measured over 10 runs for a period of 30 s per run. Extent of PEGylation, indirectly determined based on free thiol content, was measured with Ellman's Reagent (DTNB) according to manufacturer's instructions (Fisher) and scaled to be performed in a 96-well plate. Briefly, a working dilution of Ellman's reagent was prepared by diluting 50 microL of Ellman's Reagent solution (4 mg Ellman's Reagent dissolved in 1 mL of Reaction Buffer) and 2.5 mL of Reaction Buffer (0.1 M sodium phosphate, pH 8.0, containing 1 mM EDTA). Sample (20 microL), reaction buffer (200 microL), and Ellman's reagent solution (4 microL) were incubated in 96-well plate for 15 min at room temperature, and then absorbance was measured at 412 nm.

To determine any possible reactions with free amines on the surface of Gal-1, fluoraldehyde o-phthaldialdehyde (OPA) solution was used according to manufacturer's instructions (Fisher) and scaled to be performed in a black 96-well plate. Briefly, 20 microL of sample in PBS was mixed with 200 microL of OPA solution. Samples and reagent were mixed well and the fluorescence (ex/em: 360/455 nm) was measured approx-imately 1 min after mixing.

Tri-PEG-Tri Activity Studies. Tri-PEG-Tri and Tri Gal-1 were sterilized by passing through a 0.22 microm syringe filter. Jurkat T cells were plated in a 96-well plate at 20,000 cells/well. Tri Gal-1 or Tri-PEG-Tri in PBS were added to Jurkat T cell cultures at a final concentration of 0-13 microM and incubated for 18 h at 37° C., 5% CO2. Following incubation, cells were imaged with light microscopy to assess agglutination. To measure cell viability, CellTiter-Blue assay (Promega, Madison, Wis.) was used according to the manufacturer's instructions and samples were incubated for 1 h. To determine dependency of lectin activity, β-lactose was added to cell cultures at a final concentration of 10 mM prior to administration of Gal-1 treatments. Following treatment, CellTiter-Blue assay (Prom-ega, Madison, Wis.) was used as described above.

Statistical Analysis. All experimental and control groups had at least n=3 for the binding affinity, oxidative inactivation, and Jurkat T cell apoptosis studies, free thiol content, free amine content, and Jurkat T cell metabolic studies. A representative graph was shown for binding affinity studies. The oxidation inactivation and Jurkat apoptosis studies were repeated three times. Data was analyzed for statistically significant differences using one-way ANOVA with Tukey's post hoc (p=0.05) in GraphPad Prism software.

REFERENCES FOR EXAMPLE 1

(1) Toscano, M., Bianco, G., Ilarregui, J., Croci, D., Correale, J., Hernandez, J., Zwirner, N., Poirier, F., Riley, E., Baum, L., et al. (2007) Differential glycosylation of T(H)1, T(H)2 and T(H)-17 effector cells selectively regulates susceptibility to cell death. Nat. Immunol. 8, 825-834.
(2) Motran, C., Molinder, K., Liu, S., Poirier, F., and Miceli, M. (2008) Galectin-1 functions as a Th2 cytokine that selectively induces Th1 apoptosis and promotes Th2 function. Eur. J. Immunol. 38, 3015-3027.
(3) Ilarregui, J. M., Croci, D. O., Bianco, G. A., Toscano, M. A., Salatino, M., Vermeulen, M. E., Geffner, J. R., and Rabinovich, G. A. (2009) Tolerogenic signals delivered by dendritic cells to T cells through a galectin-1-driven immunoregulatory circuit involving interleukin 27 and interleukin 10. Nat. Immunol. 10, 981-991.
(4) Walzel, H., Schulz, U., Neels, P., and Brock, J. (1999) Galectin-1, a natural ligand for the receptor-type protein tyrosine phosphatase CD45. Immunol. Lett. 67, 193-202.
(5) Walzel, H., Blach, M., Hirabayashi, J., Kasai, K., and Brock, J. (2000) Involvement of CD2 and CD3 in galectin-1 induced signaling in human Jurkat T-cells. Glycobiology 10, 131-140.
(6) Pace, K., Lee, C., Stewart, P., and Baum, L. (1999) Restricted receptor segregation into membrane microdomains occurs on human T cells during apoptosis induced by galectin-1. J. Immunol. 163, 3801-3811.
(7) Elola, M., Chiesa, M., Alberti, A., Mordoh, J., and Fink, N. (2005) Galectin-1 receptors in different cell types. J. Biomed. Sci. 12, 13-29.

(8) Pace, K., Hahn, H., Pang, M., Nguyen, J., and Baum, L. (2000) Cutting edge: CD7 delivers a pro-apoptotic signal during galectin-1-induced T cell death. J. Immunol. 165, 2331-2334.

(9) Fulcher, J., Hashimi, S., Levroney, E., Pang, M., Gurney, K., Baum, L., and Lee, B. (2006) Galectin-1-matured human monocyte-derived dendritic cells have enhanced migration through extracellular matrix. J. Immunol. 177, 216-226.

(10) Thiemann, S., Man, J., Chang, M., Lee, B., and Baum, L. (2015) Galectin-1 Regulates Tissue Exit of Specific Dendritic Cell Populations. J. Biol. Chem. 290, 22662-22677.

(11) Santucci, L., Fiorucci, S., Rubinstein, N., Mencarelli, A., Palazzetti, B., Federici, B., Rabinovich, G., and Morelli, A. (2003) Galectin-1 suppresses experimental colitis in mice. Gastroenterology 124, 1381-1394.

(12) Offner, H., Celnik, B., Bringman, T., Casentiniborocz, D., Nedwin, G., and Vandenbark, A. (1990) Recombinant human beta-galactoside binding lectin suppresses clinical and histological signs of experimental autoimmune encephalomyelitis. J. Neuroimmunol. 28, 177-184.

(13) Levi, G., Tarrabhazdai, R., and Teichberg, V. (1983) Prevention and therapy with electrolectin of experimental auto-immune myasthenia-gravis in rabbits. Eur. J. Immunol. 13, 500-507.

(14) Rabinovich, G., Daly, G., Dreja, H., Tailor, H., Riera, C., Hirabayashi, J., and Chernajovsky, A. (1999) Recombinant galectin-1 and its genetic delivery suppress collagen-induced arthritis via T cell apoptosis. J. Exp. Med. 190, 385-397.

(15) Santucci, L., Fiorucci, S., Cammilleri, F., Servillo, G., Federici, B., and Morelli, A. (2000) Galectin-1 exerts immunomodulatory and protective effects on concanavalin A-induced hepatitis in mice. Hepatology 31, 399-406.

(16) Baum, L., Blackall, D., Arias-Magallano, S., Nanigian, D., Uh, S., Browne, J., Hoffmann, D., Emmanouilides, C., Territo, M., and Baldwin, G. (2003) Amelioration of graft versus host disease by galectin-1. Clin. Immunol. 109, 295-307.

(17) Toscano, M., Commodaro, A., Ilarregui, J., Bianco, G., Liberman, A., Serra, H., Hirabayashi, J., Rizzo, L., and Rabinovich, G. (2006) Galectin-1 suppresses autoimmune retinal disease by promoting concomitant Th2- and T regulatory-mediated anti-inflammatory responses. J. Immunol. 176, 6323-6332.

(18) Starossom, S., Mascanfroni, I., Imitola, J., Cao, L., Raddassi, K., Hernandez, S., Bassil, R., Croci, D., Cerliani, J., Delacour, D., et al. (2012) Galectin-1 Deactivates Classically Activated Microglia and Protects from Inflammation-Induced Neurodegeneration. Immunity 37, 249-263.

(19) Levroney, E., Aguilar, H., Fulcher, J., Kohatsu, L., Pace, K., Pang, M., Gurney, K., Baum, L., and Lee, B. (2005) Novel innate immune functions for galectin-1: Galectin-1 inhibits cell fusion by nipah virus envelope glycoproteins and augments dendritic cell secretion of proinflammatory cytokines. J. Immunol. 175, 413-420.

(20) Giudicelli, V., Lutomski, D., LeviStrauss, M., Bladier, D., JoubertCaron, R., and Caron, M. (1997) Is human galectin-1 activity modulated by monomer/dimer equilibrium? Glycobiology 7, 323.

(21) Cedeno-Laurent, F., Barthel, S., Opperman, M., Lee, D., Clark, R., and Dimitroff, C. (2010) Development of a Nascent Galectin-1 Chimeric Molecule for Studying the Role of Leukocyte Galectin-1 Ligands and Immune Disease Modulation. J. Immunol. 185, 4659-4672.

(22) Earl, L., Bi, S., and Baum, L. (2011) Galectin multimerization and lattice formation are regulated by linker region structure. Glycobiology 21, 6-12.

(23) van der Leij, J., van den Berg, A., Harms, G., Eschbach, H., Vos, H., Zwiers, P., van Weeghel, R., Groen, H., Poppema, S., and Visser, L. (2007) Strongly enhanced IL-10 production using stable galectin-1 homodimers. Mol. Immunol. 44, 506-513.

(24) Farhadi, S. A., and Hudalla, G. A. (2016) Engineering galectin-glycan interactions for immunotherapy and immunomodulation. Exp. Biol. Med. (London, U. K.) 241, 1074-83.

(25) Raghavan, M., and Bjorkman, P. (1996) Fc receptors and their interactions with immunoglobulins. Annu. Rev. Cell Dev. Biol. 12, 181-220.

(26) Nishi, N., Itoh, A., Fujiyama, A., Yoshida, N., Araya, S., Hirashima, M., Shoji, H., and Nakamura, T. (2005) Development of highly stable galectins: Truncation of the linker peptide confers protease-resistance on tandem-repeat type galectins. FEBS Lett. 579, 2058-2064.

(27) Sliepen, K., van Montfort, T., Melchers, M., Isik, G., and Sanders, R. (2015) Immunosilencing a Highly Immunogenic Protein Trimerization Domain. J. Biol. Chem. 290, 7436-7442.

(28) Lee, R., Ichikawa, Y., Allen, H., and Lee, Y. (1990) Binding characteristics of galactoside-binding lectin (galaptin) from human spleen. J. Biol. Chem. 265, 7864-7871.

(29) Guardia, C., Caramelo, J., Trujillo, M., Mendez-Huergo, S., Radi, R., Estrin, D., and Rabinovich, G. (2014) Structural basis of redox-dependent modulation of galectin-1 dynamics and function. Glycobiology 24, 428-441.

(30) Cho, M., and Cummings, R. (1995) Galectin-1, A beta-galactoside-binding lectin in chinese-hamster ovary cells. 2. local-ization and biosynthesis. J. Biol. Chem. 270, 5207-5212.

(31) Hirabayashi, J., and Kasai, K. (1991) Effect of amino-acid substitution by site-directed mutagenesis on the carbohydrate recognition and stability of human 14-kDa beta-galactoside-binding lectin. J. Biol. Chem. 266, 23648-23653.

(32) Abbott, W., and Feizi, T. (1991) Soluble 14-kDa beta-galactoside-specific bovine lectin—evidence from mutagenesis and proteolysis that almost the complete polypeptide-chain is necessary for integrity of the carbohydrate recognition domain. J. Biol. Chem. 266, 5552-5557.

(33) Tracey, B., Feizi, T., Abbott, W., Carruthers, R., Green, B., and Lawson, A. (1992) Subunit molecular mass assignment of 14,654-Da to the soluble beta-galactoside-binding lectin from bovine heart-muscle and demonstration of intramolecular disulfide bonding associated with oxidative inactivation. J. Biol. Chem. 267, 10342-10347.

(34) Inagaki, Y., Sohma, Y., Horie, H., Nozawa, R., and Kadoya, T. (2000) Oxidized galectin-1 promotes axonal regeneration in peripheral nerves but does not possess lectin properties. Eur. J. Biochem. 267, 2955-2964.

(35) Griffith, B., Pendyala, S., Hecker, L., Lee, P., Natarajan, V., and Thannickal, V. (2009) NOX Enzymes and Pulmonary Disease. Antioxid. Antioxid. Redox Signaling 11, 2505-2516.

(36) Nishi, N., Abe, A., Iwaki, J., Yoshida, H., Itoh, A., Shoji, H., Kamitori, S., Hirabayashi, J., and Nakamura, T. (2008) Functional and structural bases of a cysteine-less mutant as a long-lasting substitute for galectin-1. Glycobiology 18, 1065-1073.

(37) Stowell, S. R., Arthur, C. M., Cummings, R. D., and Feasley, C. L. (2015) Alkylation of Galectin-1 with Iodo-acetamide and Mass Spectrometric Mapping of the Sites of Incorporation. Methods Mol. Biol. 1207, 51-62.

(38) Richter, A., and Akerblom, E. (2004) Antibodies against polyethylene-glycol produced in animals by immunization with monomethoxy polyethylene-glycol modified proteins. Int. Arch. Allergy Immunol. 70, 124-131.

(39) White, C. J., and Bode, J. W. (2018) PEGylation and dimerization of expressed proteins under near equimolar conditions with potassium 2-pyridyl acyltrifluoroborates. ACS Cent. Sci. 4, 197-206.

(40) Tao, L., Kaddis, C. S., Ogorzalek Loo, R. R., Grover, G. N., Loo, J. A., and Maynard, H. D. (2009) Synthetic approach to homodimeric protein-polymer conjugates. Chem. Commun. (Cam-bridge, U. K.), 2148-2150.

(41) Lorenzo, M. M., Decker, C. G., Kahveci, M. U., Paluck, S. J., and Maynard, H. D. (2016) Homodimeric protein-polymer conjugates via the tetrazine-trans-cyclooctene ligation. Macromolecules 49, 30-37.

(42) Doherty, D., Rosendahl, M., Smith, D., Hughes, J., Chlipala, E., and Cox, G. (2005) Site-specific PEGylation of engineered cysteine analogues of recombinant human granulocyte-macrophage colony-stimulating factor. Bioconjugate Chem. 16, 1291-1298.

(43) Rosendahl, M., Doherty, D., Smith, D., Carlson, S., Chlipala, E., and Cox, G. (2005) A long-acting, highly potent interferon alpha-2 conjugate created using site-specific PEGylation. Bioconjugate Chem. 16, 200-207.

(44) Harris, J., and Chess, R. (2003) Effect of pegylation on pharmaceuticals. Nat. Rev. Drug Discovery 2, 214-221.

(45) Long, D., Doherty, D., Eisenberg, S., Smith, D., Rosendahl, M., Christensen, K., Edwards, D., Chlipala, E., and Cox, G. (2006) Design of homogeneous, monopegylated erythropoietin analogs with preserved in vitro bioactivity. Exp. Hematol. 34, 697-704.

(46) Mittal, M., Siddiqui, M., Tran, K., Reddy, S., and Malik, A. (2014) Reactive Oxygen Species in Inflammation and Tissue Injury. Antioxid. Antioxid. Redox Signaling 20, 1126-1167.

(47) Brandt, B., Buchse, T., Abou-Eladab, E., Tiedge, M., Krause, E., Jeschke, U., and Walzel, H. (2008) Galectin-1 induced activation of the apoptotic death-receptor pathway in human Jurkat T lymphocytes. Histochem. Cell Biol. 129, 599-609.

(48) Tartier, L., McCarey, Y., Biaglow, J., Kochevar, I., and Held, K. (2000) Apoptosis induced by dithiothreitol in HL-60 cells shows early activation of caspase 3 and is independent of mitochondria. Cell Death Differ. 7, 1002-1010.

(49) Uchida, K. (2003) Histidine and lysine as targets of oxidative modification. Amino Acids 25, 249-257.

(50) Restuccia, A., Tian, Y. F., Collier, J. H., and Hudalla, G. A. (2015) Self-assembled glycopeptide nanofibers as modulators of galectin-1 bioactivity. Cell. Mol. Bioeng. 8, 471-487.

Example 2

Figure 10:
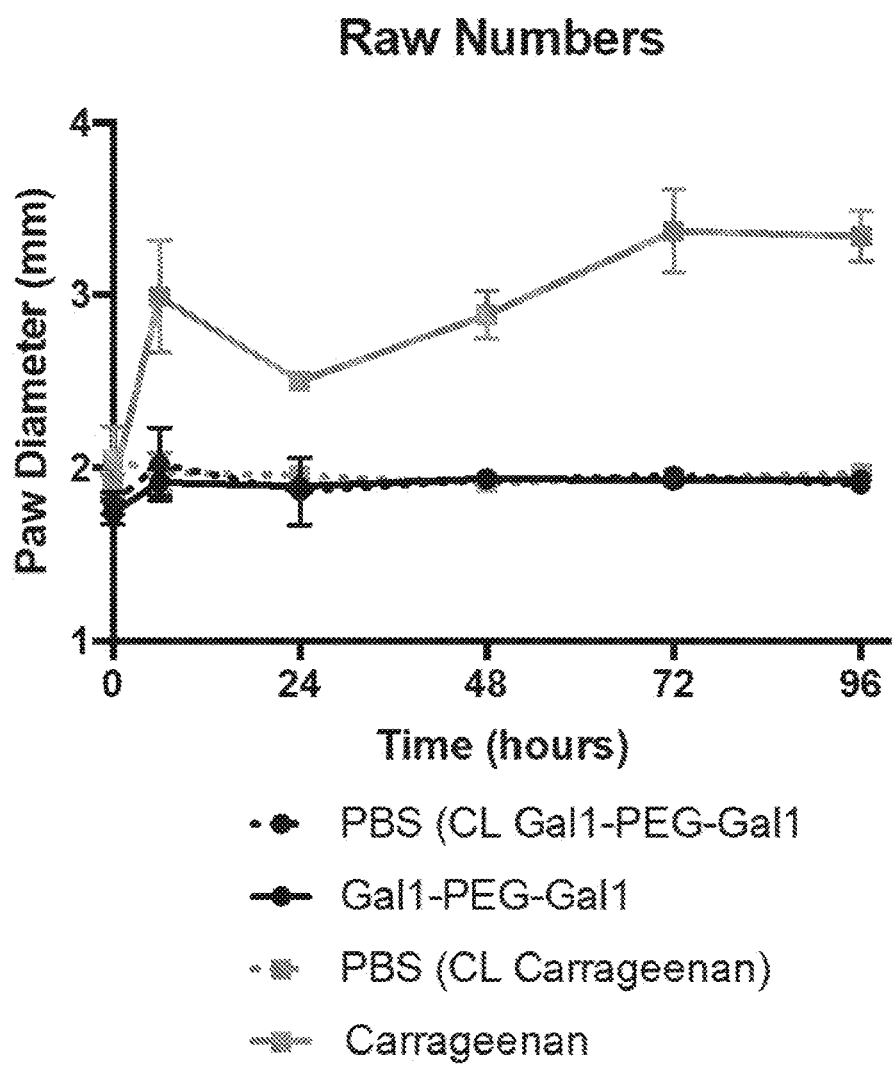
FIG. 10 shows a graph that can demonstrate that the modified Gal-1 proteins described herein do not generate inflammation on their own in a Carrageenan model of inflammation. Following anesthetization, animals were injected subcutaneously into the top of one hind paw with a saline solution containing 50 microL Carrageenan (1% w/v), 50 microL of 3 microg Tet Gal1, or 50 microL 3 microg TriGal1-PEG-TriGal1, 50 microL saline was injected into the contralateral (CL) paw. Local edema was quantified using calipers on day 0 (before injection), day 0 (6 h after injection), day 1, 2, 3, and 4.
Figure 11:
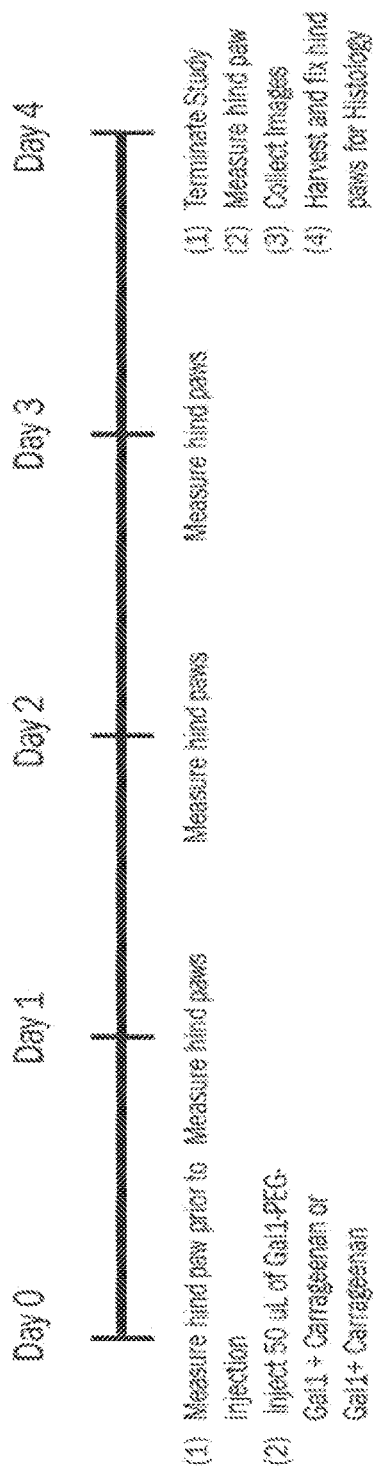
FIG. 11 shows a schematic of an experiment to determine the effect of treatment with modified Gal-1 proteins as described herein on inflammation in an in vivo Carrageenan model of inflammation.
Figure 12:
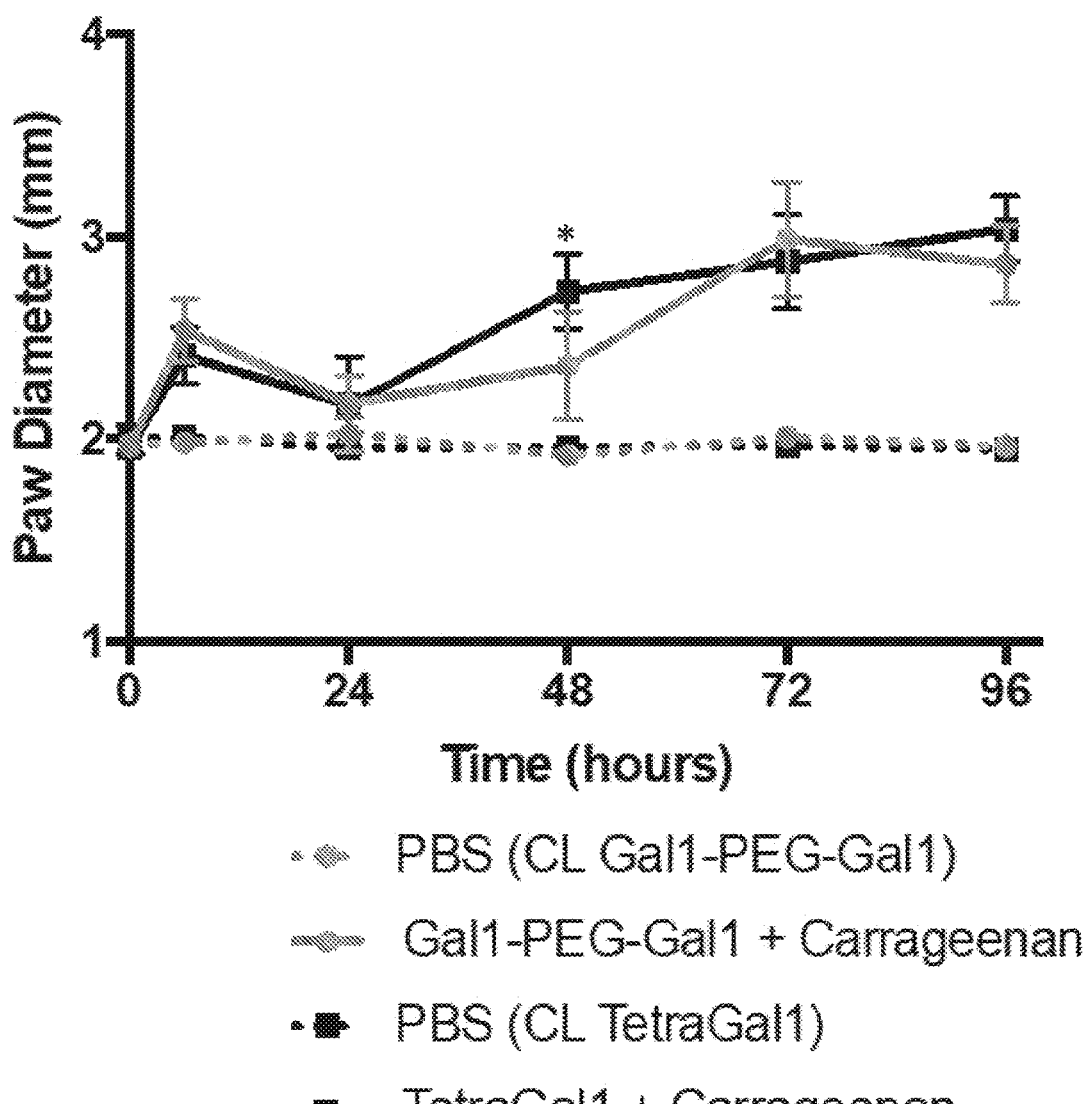
FIG. 12 shows a graph demonstrating the results of treatment of inflammation in a Carrageenan model of inflammation with various modified Gal-1 proteins described herein. In this model, 25 μL of 2% Carrageenan in phosphate buffered saline (PBS) and 25 μL of 3 μg of total modified Gal-1 protein (mixed together in one injection) was injected into a paw and the size of the paw was measured and used to determine the effect on inflammation.
Figure 13:
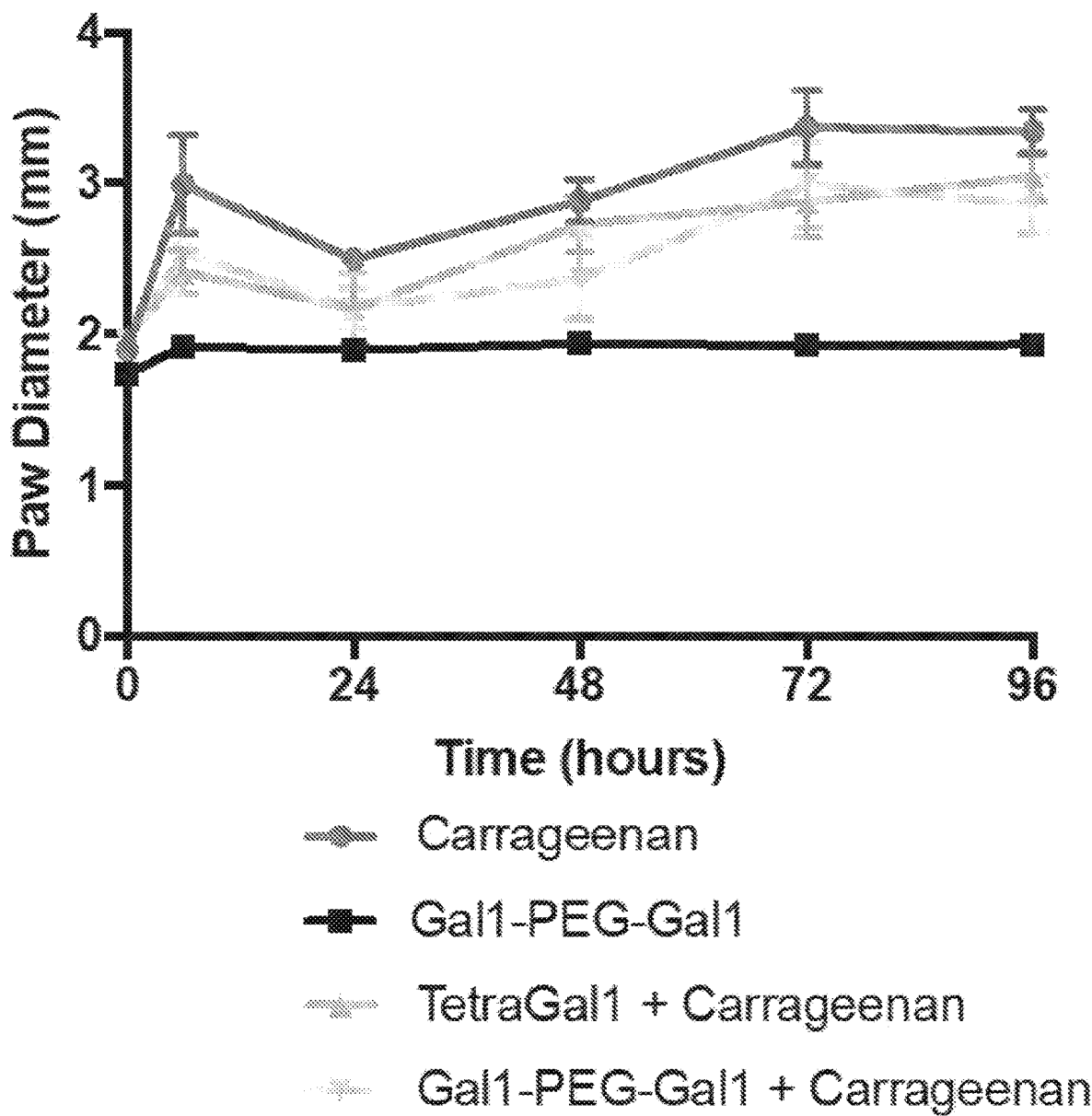
FIG. 13 shows a graph demonstrating the combined results of treatment of inflammation in a Carrageenan model of inflammation with various modified Gal-1 proteins described herein. In this model, 25 μL of 2% Carrageenan in phosphate buffered saline (PBS) and 25 μL of 3 μg of total modified Gal-1 protein (mixed together in one injection) was injected into a paw and the size of the paw was measured and used to determine the effect on inflammation.
Figure 14A:
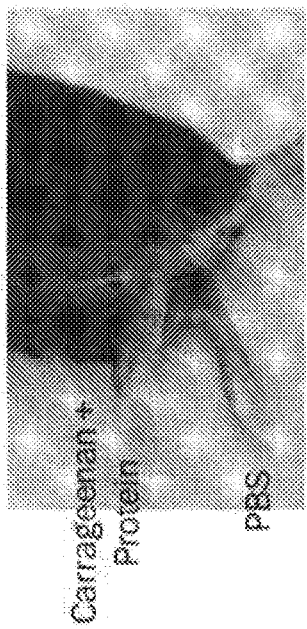
FIGS. 14A-14D show photographic images of hind limbs injected as described with respect to FIG. 13.
Figure 14A:
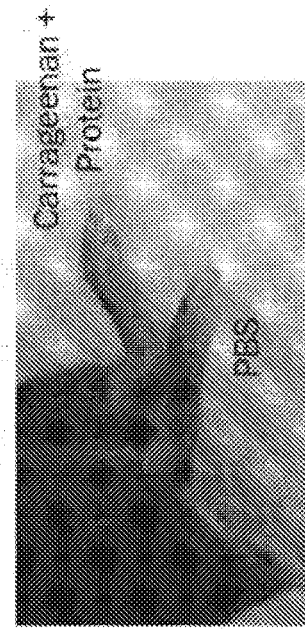
Figure 14B:
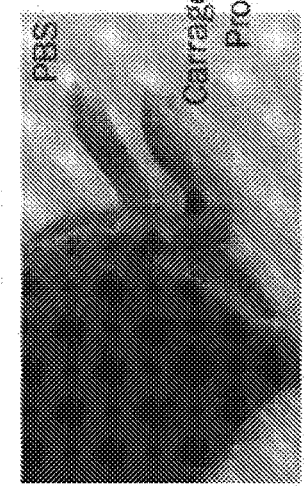
Figure 14C:
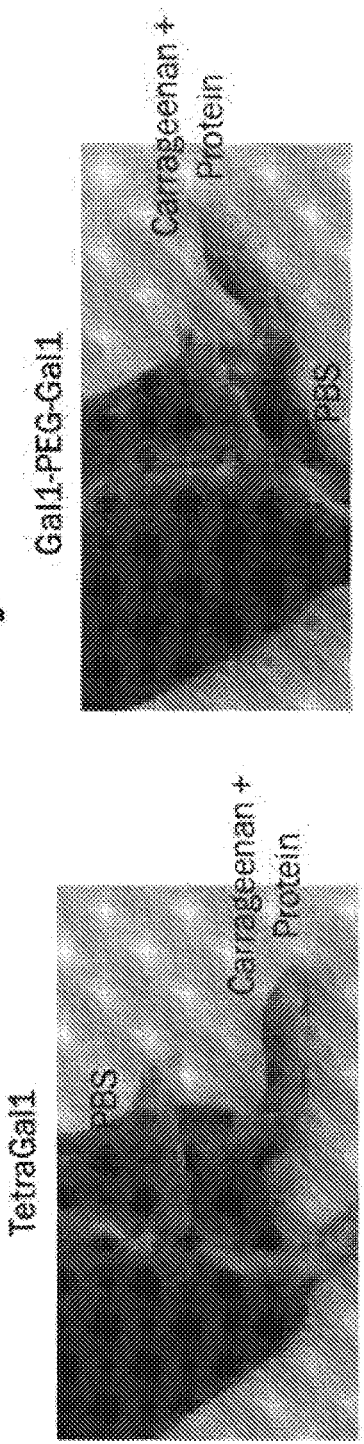
Figure 14D:
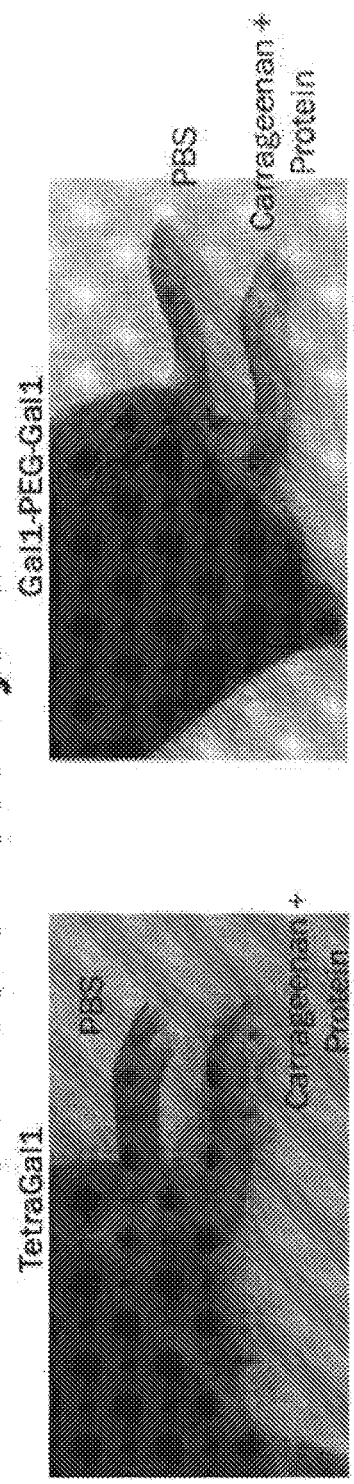

This Example can demonstrate, inter alia, the in vivo effect on inflammation of various modified Gal-1 polypeptides. FIG. 10 shows a graph that can demonstrate that the modified Gal-1 proteins described herein do not generate inflammation on their own in a Carrageenan model of inflammation. Following anesthetization, animals were injected subcutaneously into the top of one hind paw with a saline solution containing 50 microL Carrageenan (1% w/v), 50 microL of 3 microg Tet Gal1, or 50 microL 3 microg TriGal1-PEG-TriGal1. 50 microL saline was injected into the contralateral (CL) paw. Local edema can be quantified using calipers on day 0 (before injection), day 0 (6 h after injection), day 1, 2, 3, and 4. FIG. 11 shows a schematic depicting the timeline of an experiment to determine the effect of treatment with modified Gal-1 proteins as described herein on inflammation in an in vivo Carrageenan model of inflammation. FIG. 12 shows a graph demonstrating the results of treatment of inflammation in a Carrageenan model of inflammation with various modified Gal-1 proteins described herein. In this model, 25 µL of 2% Carrageenan in phosphate buffered saline (PBS) and 25 µL of 3 µg of total modified Gal-1 protein (mixed together in one injection) was injected into a paw and the size of the paw was measured and used to determine the effect on inflammation. The co-injection of Gal1 and Carrageen is to determine the protein's effect on carrageenan induced inflammation and edema. Previous results suggest Gal1 can ameliorate the first phase of carrageenan induced inflammation. FIG. 13 shows a graph demonstrating the combined results of treatment of inflammation in a Carrageenan model of inflammation with various modified Gal-1 proteins described herein. In this model, 25 µL of 2% Carrageenan in phosphate buffered saline (PBS) and 25 µL of 3 µg of total modified Gal-1 protein (mixed together in one injection) was injected into a paw and the size of the paw was measured and used to determine the effect on inflammation. FIGS. 14A-14D show photographic images of hind limbs injected as described with respect to FIG. 13. These data can suggest the PEGylated variant is at least as effective and the monomeric variant lacking surface cysteines and not PEGylated.

Example 3

Figure 15:
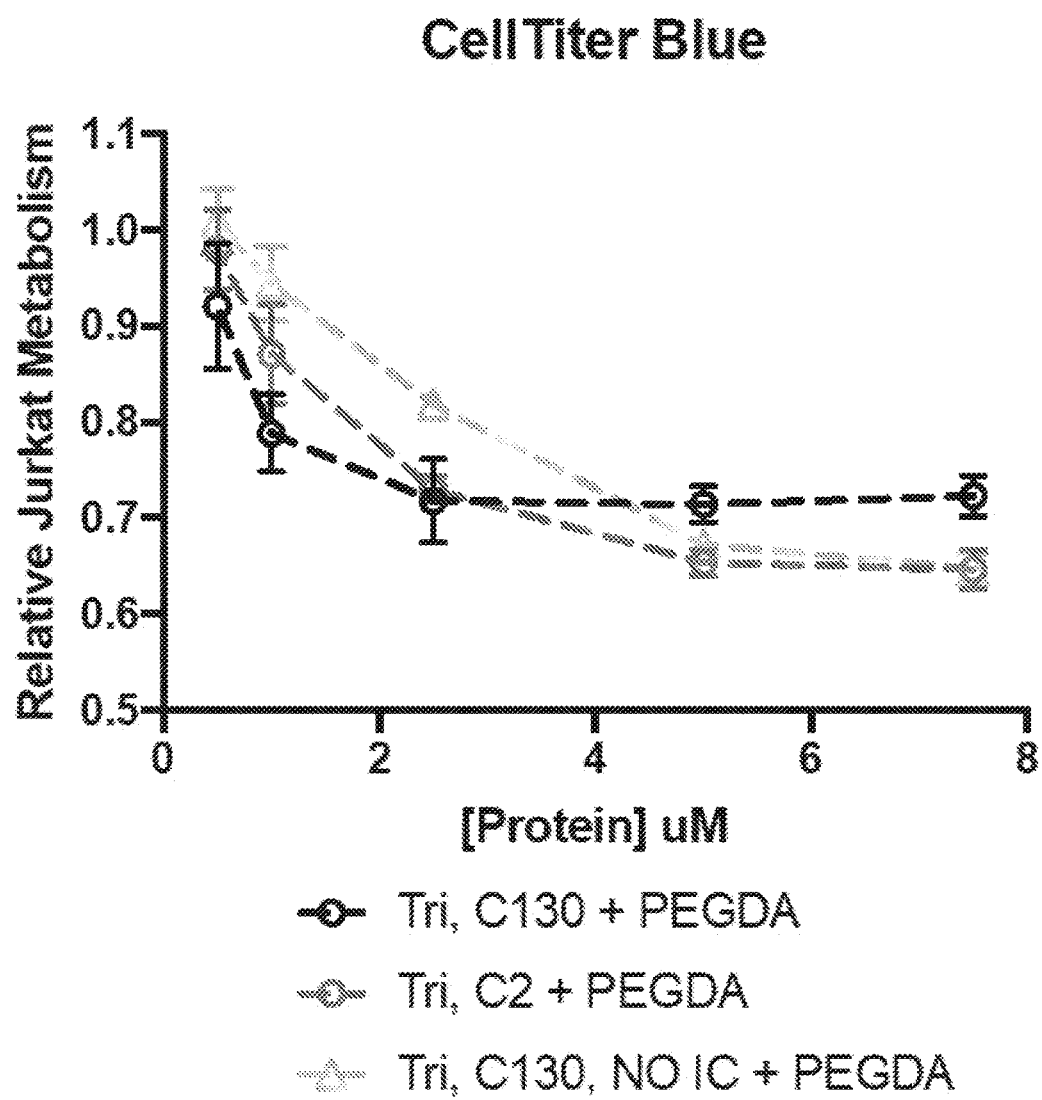
FIG. 15 shows a graph demonstrating the effect of PEGylation with Acrylate at varying residues a mutated Gal-1.
Figure 16:
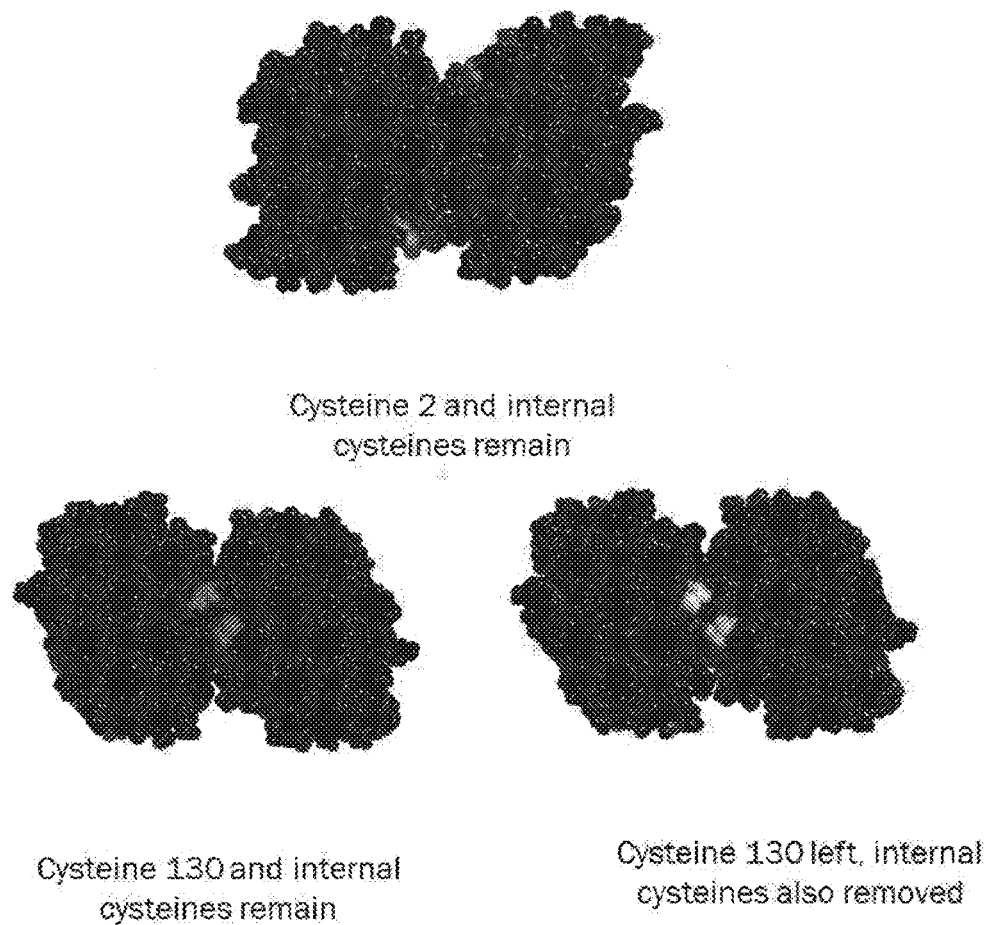
FIG. 16 shows computer models of the modified Gal-1 proteins in FIG. 15 that can demonstrate the 3-D positioning of the residue modified with PEGylation and Acrylate.
Figure 17:
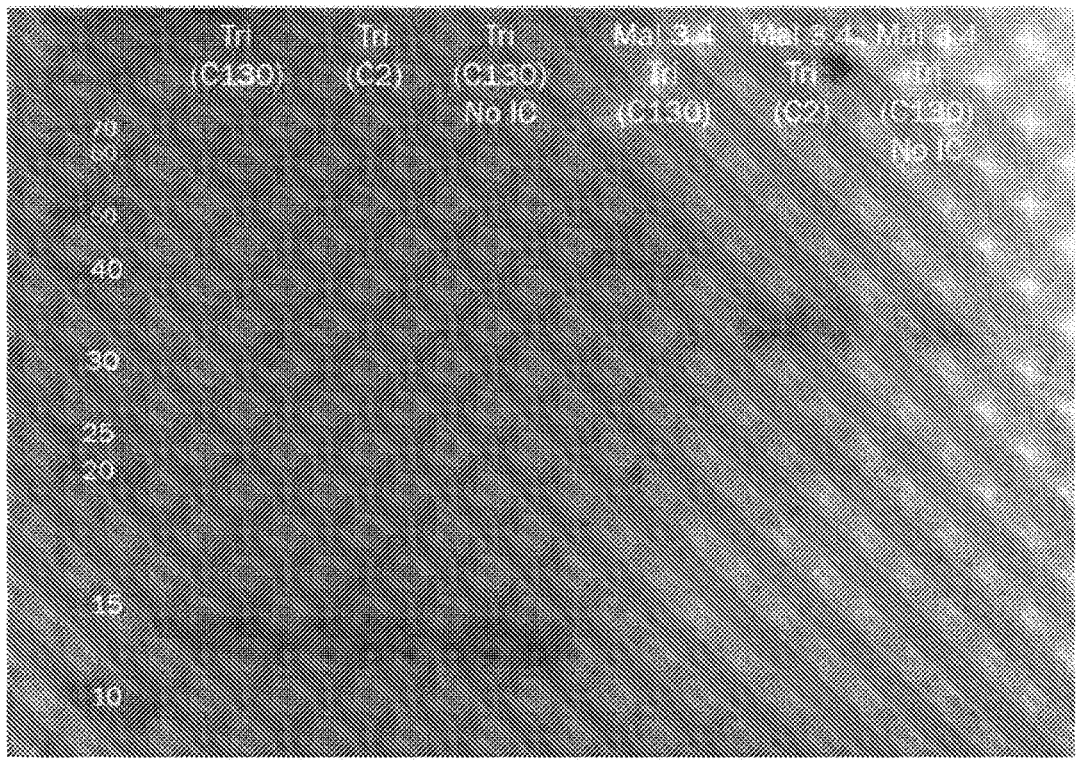
FIG. 17 shows a scan of a SDS-PAGE gel that can demonstrate PEGylation with D-MAL (in place of Acrylate) (Gal-PEGmal) on a modified Gal-1 protein. PEG-Dmal MW was 3.4 kDa.
Figure 18:
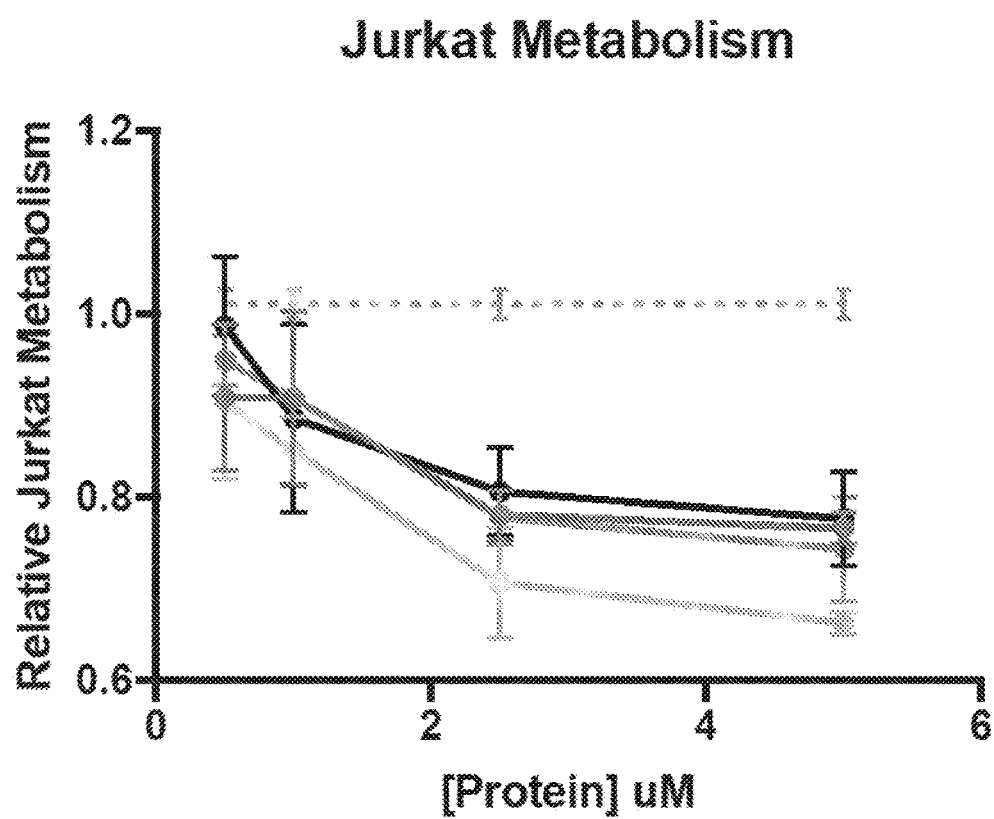
FIG. 18 shows a graph that can demonstrate the effect of Gal-PEGmal on Jurkat Metabolism. The lightest grey line at the bottom is the C130 variant "Tri".
Figure 19:
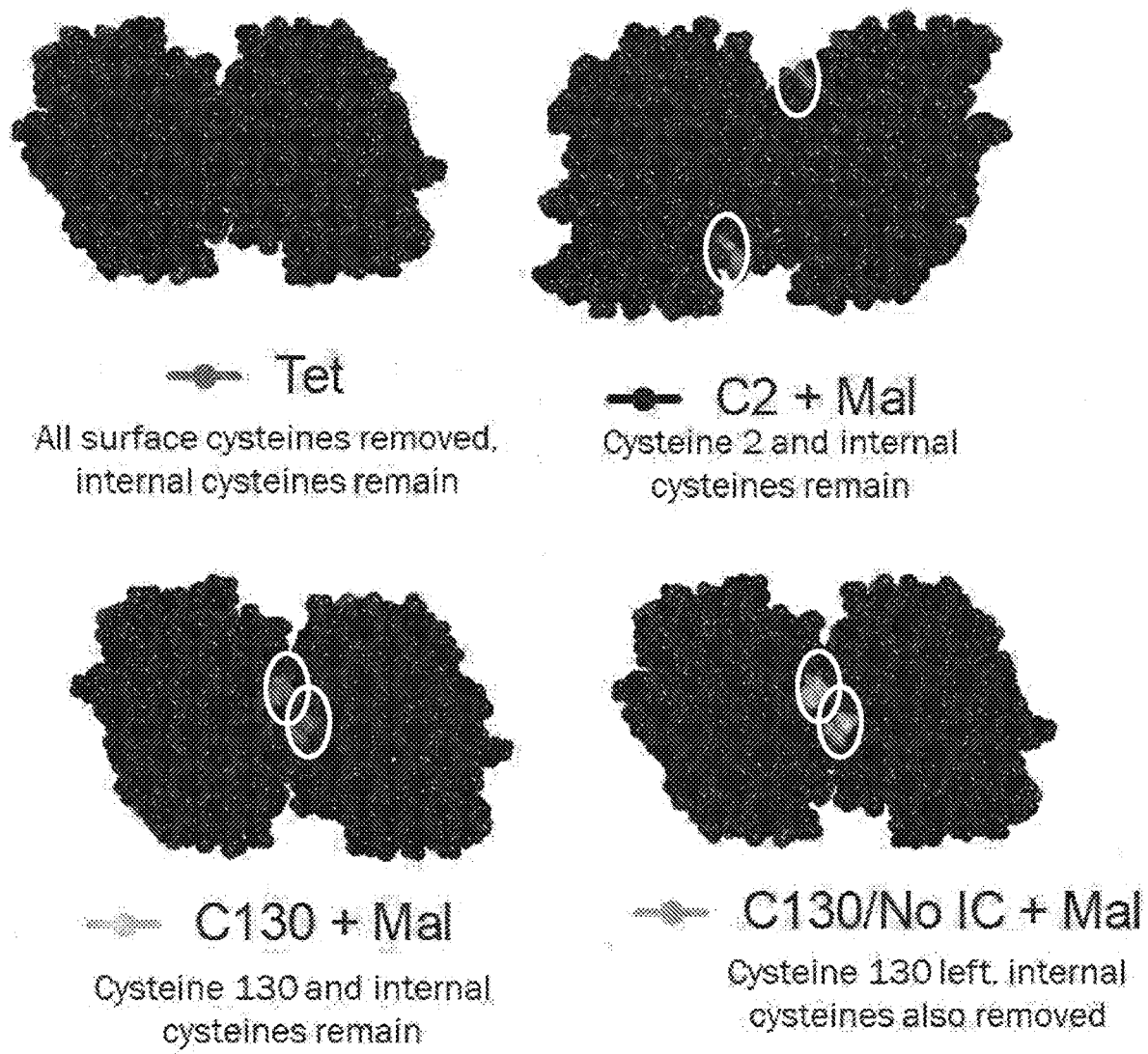
FIG. 19 show computer models of the modified Gal-1 proteins in FIG. 19 the effect of D-mal PEGylation on the 3D positioning of residues modified with D-mal PEGylation.

In addition to the C130, other sites can be modified with PEGylation with Acrylate. FIG. 15 shows a graph demonstrating the effect of PEGylation with Acrylate at varying residues a mutated Gal-1. This assay was conducted by mixing 20,000 Jurkat T cells with a final concentration of 5 microM protein. After an overnight incubation, Jurkat T Cell metabolism was measured with CellTiter Blue according to the manufacturer instructions. The results are plotted. Activity of Gal-1 PEGylated at C2 with acrylate is comparable to the activity Gal-1 PEGylated at C130. Gal-1 PEGylated at C130 for the variant lacking internal Cys residues (No IC) does not have improved activity compared to the other variants. FIG. 16 shows computer models of the modified Gal-1 proteins in FIG. 15 that can demonstrate the 3-D positioning of the residue modified with PEGylation and Acrylate. Further other PEGylations beyond Acrylate can be done. For Example, Di-MAL PEGylation can be used instead of Acrylate. FIG. 17 shows a scan of an SDS-PAGE gel that demonstrates PEGylation with D-MAL (in place of Acrylate) (Gal-PEGmal) on a modified Gal-1 protein. FIG. 18 shows that Gal-1 variants reacted with Di-Mal are more active for decreasing Jurkat T cell metabolic activity (light gray line) than Gal-1 variants that are not PEGylated. This experiment was conducted as described above for FIG. 15. FIG. 19 shows computer models of the modified Gal-1 proteins in FIG. 15 that can demonstrate the 3-D positioning of the residue modified with PEGylation and Mal.

We claim:

1. A modified gal1 polypeptide comprising:
   at least three amino acid mutations as compared to SEQ ID NO: 1, wherein the at least three amino acid mutations comprise three mutations selected from the group consisting of: C2S, C16S, C88S, and C130S, and wherein at least one of the cysteine residues selected from C2, C16, C88, and C130 is unmodified.

2. The modified gal1 polypeptide of claim 1, wherein the at least three amino acid mutations comprise C2S, C16S, and C88S, and wherein C130 is unmodified.

3. The modified gal1 polypeptide of claim 1, wherein the modified gal1 polypeptide is resistant to oxidative environments.

4. The modified gal1 polypeptide of claim 3, wherein the modified gal1 polypeptide has an amino acid sequence that is 90-100% identical to SEQ ID NO: 7.

5. The modified gal1 polypeptide of claim 1, wherein the modified gal1 polypeptide has an amino acid sequence that is 90-100% identical to SEQ ID NO: 7.

6. A pharmaceutical formulation comprising a modified gal1 polypeptide as in claim 1 and a pharmaceutically acceptable carrier.

7. A method comprising:
   administering an amount of a modified gal1 polypeptide as in claim 1 to a subject.

8. The method of claim 7, wherein the subject has an inflammatory disease, chronic inflammatory disease, autoimmune disease, or a symptom thereof.

9. A polynucleotide comprising a sequence that encodes a modified gal1 polypeptide as in claim 1.

10. The polynucleotide of claim 9, wherein the polynucleotide is about 98 to about 100 percent identical to SEQ ID NO: 8.

11. The modified gal1 polypeptide of claim 1, wherein the modified gal1 polypeptide has an amino acid sequence that is 100% identical to SEQ ID NO: 11.

12. A modified gal1 dimer comprising two crosslinked modified gal1 polypeptides of claim 1.

13. A modified gal1 tetramer comprising four crosslinked modified gal1 polypeptides of claim 1.

14. A pharmaceutical formulation comprising the modified gal1 dimer of claim 12 and a pharmaceutically acceptable carrier.

15. A pharmaceutical formulation comprising the modified gal1 tetramer of claim 13 and a pharmaceutically acceptable carrier.

16. A method comprising administering the modified gal1 dimer of claim 12 to a subject.

17. A method comprising administering the modified gal1 tetramer of claim 13 to a subject.

18. The method of claim 16, wherein the subject has an inflammatory disease, chronic inflammatory disease, autoimmune disease, or a symptom thereof.

19. The method of claim 17, wherein the subject has an inflammatory disease, chronic inflammatory disease, autoimmune disease, or a symptom thereof.

* * * * *